(12) United States Patent
Lukehart et al.

(10) Patent No.: US 8,088,352 B2
(45) Date of Patent: Jan. 3, 2012

(54) GRAPHITIC-CARBON-NANOFIBER/POLYMER BRUSHES AS GAS SENSORS

(75) Inventors: Charles Martin Lukehart, Nashville, TN (US); Lang Li, York, PA (US)

(73) Assignee: Vanderbilt University, Nashville, TN (US)

( * ) Notice: Subject to any disclaimer, the term of this patent is extended or adjusted under 35 U.S.C. 154(b) by 258 days.

(21) Appl. No.: 11/998,470

(22) Filed: Nov. 28, 2007

(65) Prior Publication Data

US 2008/0257015 A1    Oct. 23, 2008

Related U.S. Application Data

(60) Provisional application No. 60/861,252, filed on Nov. 28, 2006.

(51) Int. Cl.
*D01F 9/12* (2006.01)
*C08K 9/00* (2006.01)
(52) U.S. Cl. .................. 423/447.1; 423/447.2; 523/215
(58) Field of Classification Search .................. 523/215; 423/447.1, 447.2
See application file for complete search history.

(56) References Cited

U.S. PATENT DOCUMENTS

| 7,060,241 B2 * | 6/2006 | Glatkowski | 423/447.1 |
| 2004/0223900 A1 * | 11/2004 | Khabashesku et al. | 423/447.1 |
| 2006/0217482 A1 * | 9/2006 | Lukehart et al. | 524/495 |

OTHER PUBLICATIONS

Qin et al, J. Am. Chem. Soc. 2004, 126 170-176.*
Li et al., Chem Mater., 2006, 18, 94-99, published on web Nov. 30, 2005.*

* cited by examiner

*Primary Examiner* — Vickey Nerangis
(74) *Attorney, Agent, or Firm* — John Bruckner PC

(57) ABSTRACT

A composition of matter including at least one graphitic-carbon-nanofiber/polymer brush. A method of making the graphitic-carbon-nanofiber/polymer brush includes covalently bonding a polymer to a surface of a graphitic-carbon-nanofiber by atom-transfer-radical-polymerization. An apparatus includes an analyte sensor including at least one graphitic-carbon-nanofiber/polymer brush. A method includes detecting an analyte including exposing at least one graphitic-carbon-nanofiber/polymer brush to the analyte.

3 Claims, 21 Drawing Sheets

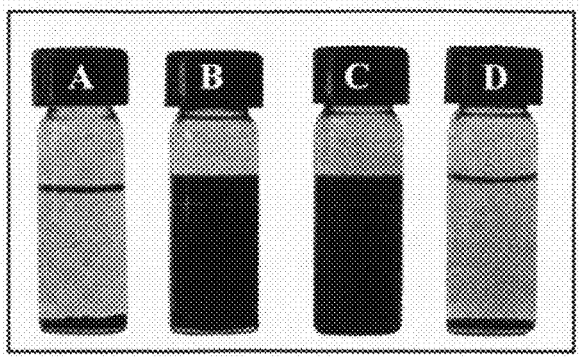
FIG. 13
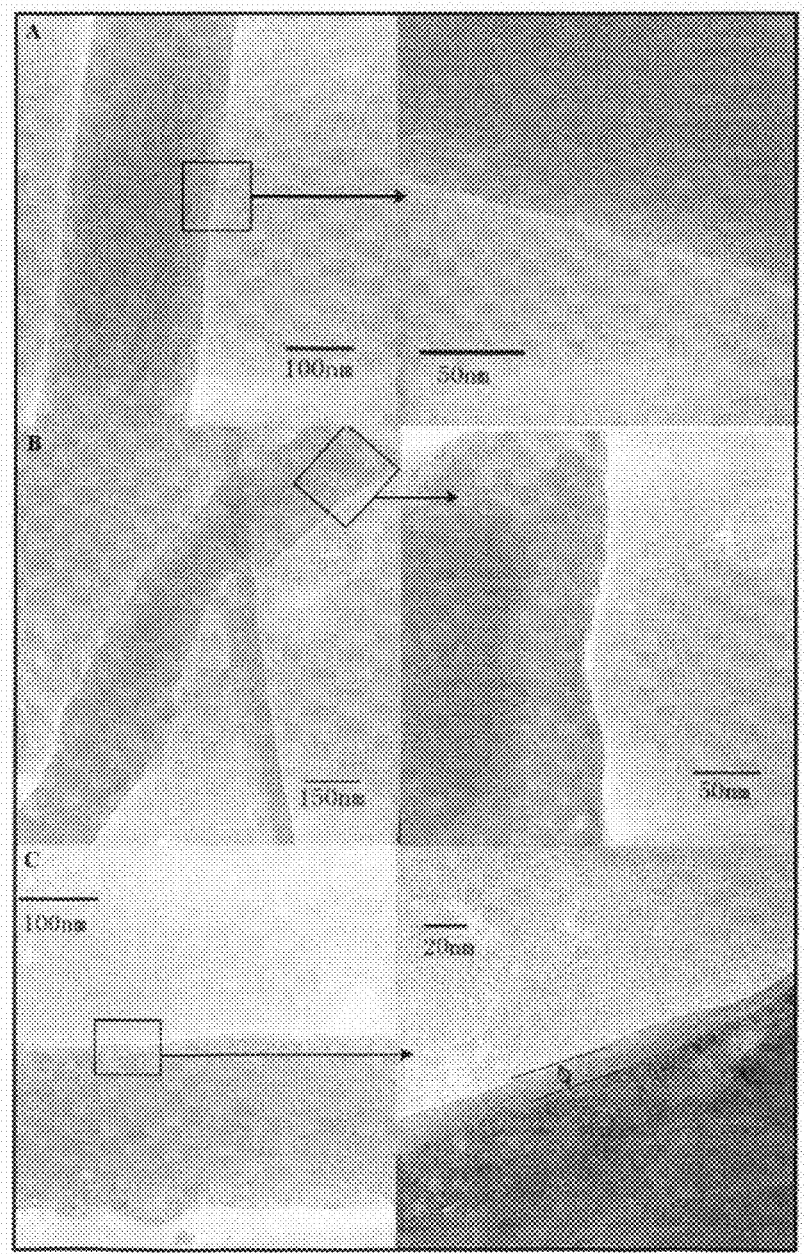
FIG. 15A-C

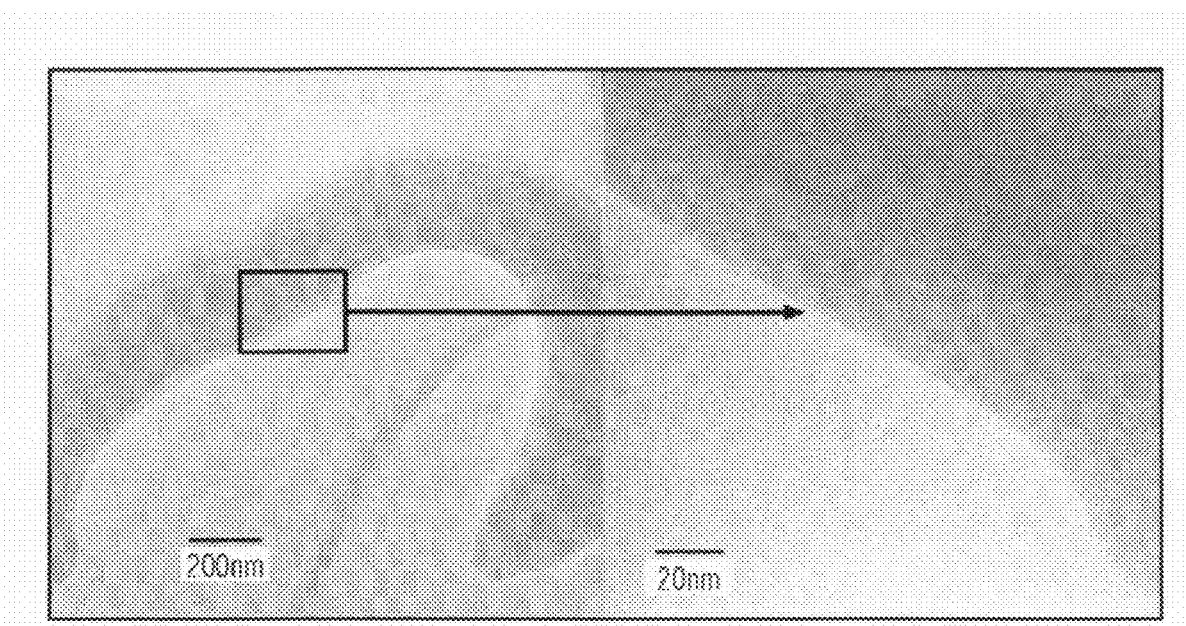
FIG. 22A-B
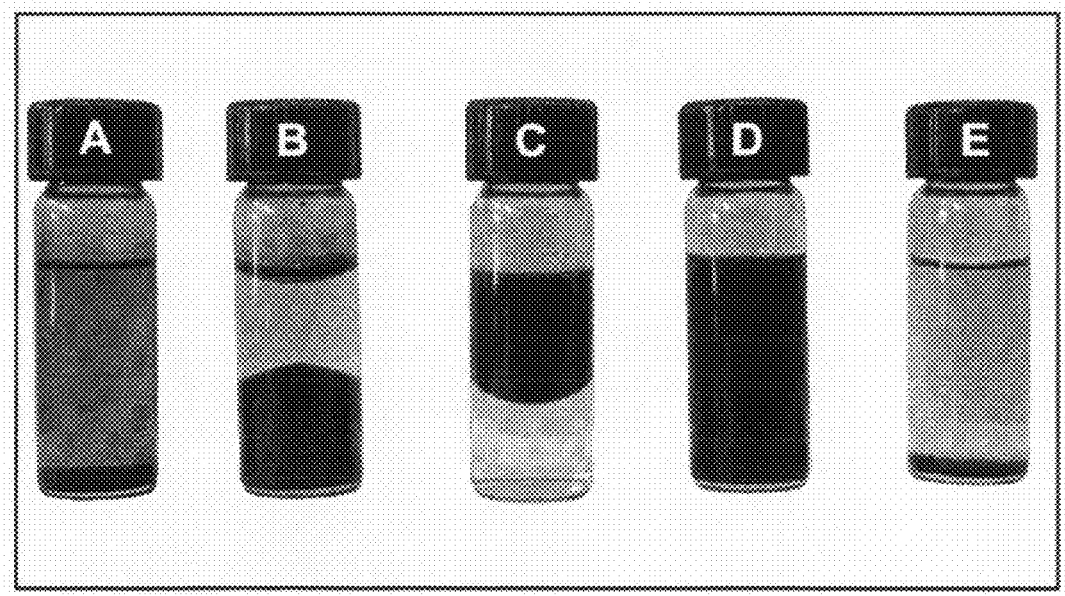
FIG. 23

GRAPHITIC-CARBON-NANOFIBER/POLYMER BRUSHES AS GAS SENSORS

CROSS-REFERENCE TO RELATED APPLICATION

This application claims a benefit of priority under 35 U.S.C. 119(e) from copending provisional patent application U.S. Ser. No. 60/861,252, filed Nov. 28, 2006, the entire contents of which are hereby expressly incorporated herein by reference for all purposes.

STATEMENT AS TO RIGHTS TO INVENTIONS MADE UNDER FEDERALLY-SPONSORED RESEARCH OR DEVELOPMENT

The present invention was at least partially the result of work performed under the following federal grants: U.S. Army Research Office W911NF-04-2-0023 (C.M.L. & L.L.) and National Science Foundation CTS-0210366 (C.M.L. & L.L.) The U.S. Government has certain rights to the invention described herein.

BACKGROUND OF THE INVENTION

Polymer brush composites comprising polymers bonded to solid substrates are known in the prior art as evidenced by the disclosures in U.S. Pat. Nos. 6,833,276; 6,780,492 and 6,423,465.

Interest in developing carbon nanostructures appropriately surface-derivatized for diverse applications remains high. Considerable progress has been made in controlling the dispersibility and wettability properties of single-walled (SWNTs) or multi-walled (MWNTs) carbon nanotubes through either covalent or non-covalent surface derivatization. [Sinani et al, *J. Am. Chem. Soc.* 2005, 127, 3463; Zhao et al, *J. Am. Chem. Soc.* 2005, 127, 8197; Niyogi et al, *Ace. Chem. Res.* 2002, 35, 1105].

Most recently, radical initiator functional groups appropriate for effecting in situ atom-transfer-radical-polymerization (ATRP) have been grafted to surface sites on SWNTs or MWNTs to form SWNT/poly(n-butyl methacrylate), SWNT/polystyrene, SWNT/poly(methyl methacrylate), SWNT/poly(tert-butyl acrylate), SWNT/poly(acrylic acid), MWNT/poly(methyl methacrylate), and MWNT/poly(methyl methacrylate)$_x$(hydroxyethyl methacrylate)$_y$ as polymer brushes having either hydrophobic or hydrophilic surfaces [Qin et al, *J. Am. Chem. Soc.* 2004, 126, 170; Qin et al, *Macromolecules* 2004, 37, 752; Kong et al, *J. Am. Chem. Soc.* 2004, 126, 412; Yao et al, *J. Am. Chem. Soc.* 2003, 125, 16015].

ATRP methods have also been used to extend polymer chains within carbon nanotube/polymer brushes [Baskaran et al, *Angew. Chem., Int. Ed. Engl.* 2004, 43, 2138; Kong et al, *J. Mater. Chem.* 2004, 14, 1401].

Graphitic carbon nanofibers (GCNFs) represent a class of nanostructured carbon fibers having atomic structures uniquely different from that of carbon nanotubes [Rodriguez et al, *Langmuir* 1995, 11, 3862; Mowles, E. D. *Surface Functionalization of VGCNFs with PendantAmino Groups*, M.S. thesis, Vanderbilt University, 2001]. Herringbone GCNFs possess canted graphene sheets (also described as geodesic-like conical graphene sheets) stacked in a nested fashion along the long fiber axis. GCNFs of this type can be prepared having average diameters from 25 nm-200 nm and lengths on the micron scale. The graphitic atomic structure of herringbone GCNFs gives a carbon nanofiber long-axis surface comprised of $C(sp^2)$ edge sites, usually passivated by hydrogen atoms.

The surface-functionalization of herringbone GCNFs with reactive linker molecules using surface oxidation and carboxyl group coupling chemistry occurs without degradation of the structural integrity of the GCNF backbone and affords surface-derivatized GCNFs having a high surface density of functional groups [Zhong et al, *Polym. Compos.* 2005, 26, 128]. Covalent binding of such linker molecules to either polymer resins or ceramic condensation oligomers gives GCNF/polymer or GCNF/ceramer hybrid materials [Zhong et al, *Polym. Compos.* 2005, 26, 128; Li et al, *Compos. Interfaces* 2004, 11, 525; Xu et al, *J. Compos. Mater.* 2004, 38, 1563].

SUMMARY OF THE INVENTION

It is an object of the present invention to provide novel graphitic carbon nanofiber (GCNF)/polymer brushes.

It is a further object of the invention to provide a novel method for synthesizing graphitic carbon nanofiber (GCNF)/polymer brushes.

The above and other objects are realized by the present invention, one embodiment of which relates to either hydrophobic or hydrophilic graphitic carbon nanofiber (GCNF)/polymer brushes, preferably prepared by atom-transfer-radical polymerization (ATRP) using the "grafted-from" synthesis strategy.

BRIEF DESCRIPTION OF THE DRAWINGS

The drawings accompanying and forming part of this specification are included to depict certain embodiments of the invention. A clearer concept of embodiments of the invention, and of components combinable with embodiments of the invention, and operation of systems provided with embodiments of the invention, will be readily apparent by referring to the exemplary, and therefore nonlimiting, embodiments illustrated in the drawings (wherein identical reference numerals (if they occur in more than one view) designate the same elements). Embodiments of the invention may be better understood by reference to one or more of these drawings in combination with the following description presented herein. It should be noted that the features illustrated in the drawings are not necessarily drawn to scale.

FIG. 13 illustrates dispersibility of (A) GCNF-$CO_2H$ sample in chloroform, (B) GCNF-PBA3 sample in chloroform, (C) GCNF-PBA3 sample in toluene, (D) GCNF-PBA3 sample in methanol. Concentration of the dispersions is about 2.5 mg/mL.

FIGS. 15A-C illustrate TEM images of (A) as-prepared GCNFs and (B), (C) GCNF-PBA3 samples.

FIGS. 22A-B illustrate TEM images of individual GCNF-PiBMA carbon nanofiber.

FIG. 23 illustrates dispersibility of (A) GCNF-$CO_2H$ sample in $CHCl_4$, (B), (C), (D) (E) GCNF-PiBMA sample in $H_2O$/$CCl_4$, toluene/$H_2O$, acetone, and methanol, respectively; where concentration of the dispersions is about 2.5 mg/mL.

DETAILED DESCRIPTION OF THE INVENTION

Figure 1:
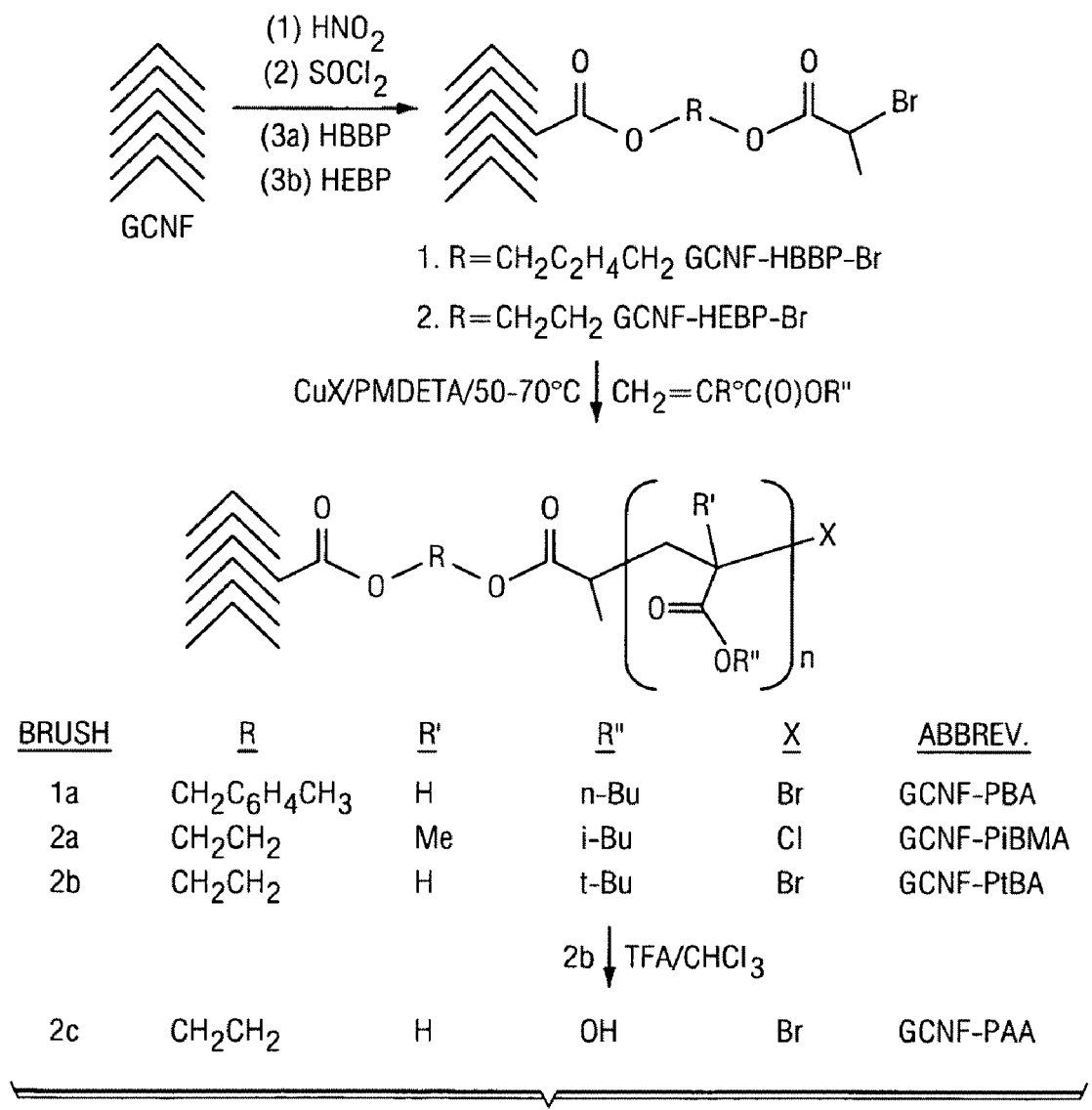
FIG. 1 illustrates a process for the synthesis of GCNF-polymer brushes.

The present invention is predicated on the discovery that a greater complexity of functional group derivatization can be produced by grafting organic polymers to GCNF surface sites to give GCNF/polymer brushes having tunable dispersibilities and surface reactivity.

It will be recognized by those skilled in the art that the present invention is amenable to the preparation of a wide variety of GCNF/polymer materials.

According to the present invention, graphitic carbon nanofiber (GCNF)/polymer brushes are prepared by atom-transfer-radicalpolymerization (ATRP) using the "grafted-from" synthesis strategy. Preferably, herringbone GCNFs are employed. Polymerization of acrylate esters is conducted at surface sites covalently derivatized with ATRP initiators to form, for example, hydrophobic composites such as GCNF/poly(n-butyl acrylate) [GCNF-PBA], GCNF/poly(iso-butyl methacrylate) [GCNF-PiBMA], GCNF/poly(tert-butyl acrylate) [GCNF-PtBA], and hydrophilic brushes such as GCNF/poly(acrylic acid) [GCNF-PAA]. Moreover, acid hydrolysis of the GCNF/acrylate/methacrylate) polymer brushes also yields hydrophilic GCNF/poly(acrylic/methacrylic acid) polymer brushes. The "grafted-from" approach in which a radical initiator, such as (4-hydroxymethyl)-benzyl 2bromopropionate (HBBP) or 2-hydroxyethyl-2'-bromopropionate (HEBP), is covalently coupled to surface carboxylic acid sites of oxidized GCNFs, GCNF-$CO_2H$ is adopted from Wang et al, *J. Am. Chem. Soc.* 1995, 117, 5614.

Solution dispersibilities of the GCNF/polymer brushes are controlled by the solubility properties of the polymer brush component with GCNF/poly(acrylate ester) brushes being hydrophobic, while the GCNF/poly(acrylic acid) brush is hydrophilic. Because of the unique atomic structure of GCNFs, a high surface density (ca. 3 chains/10 $nm^2$ of GCNF surface) of polymer brush functionalization is realized.

It will be recognized by those skilled in the art that the present invention is amenable to the preparation of a wide variety of GCNF/polymer materials.

In the following examples, transmission electron microscopy (TEM) was performed on a Philips CM-20T Electron Microscope operated at 200 KeV. $^1$HNMR spectra were recorded on a Bruker AC300 Fourier Transform Spectrometer, using $CDCl_3$ as solvent. Infrared spectra (IR) were obtained from KBr pressed pellets with an ATI Mattson Genesis Series FT-IR spectrometer. Thermogravimetric analyses (TGA) were performed on a Thermal Analysis Instruments High-Resolution TGA 2950 Thermogravimetric Analyzer. Elemental analysis was performed. BET surface area analysis was carried out on a NOVA 1000 High Speed Surface Area & Pore Size Analyzer with nitrogen gas as the absorbent. Atomic force microscopy (AFM) images were taken with a Digital Instruments Multimode IDa Nanoscope SPM in the tapping mode. Polymer molecular weights and polydispersity measurements were obtained by GPC-MALLS analysis.

Example 1

Synthesis of (4-Hydroxymethyl)-Benzyl 2-Bromopropionate (HBBP)

A 500-mL round-bottomed flask was charged with 13.06 g (94.5 mmol) of 1,4-benzenedimethanol, 20 mL (0.145 mol) TEA, 0.24 g (2.0 mmol) DMAP and 200 mL anhydrous THF. The solution was cooled to 0° C. and a solution of 10 mL (94.5 mmol) of 2-bromopropionyl bromide dissolved into 20 mL of anhydrous THF was added dropwise under nitrogen at 0° C. over 2 h. Then, the reaction mixture was raised to 40° C. and stirred for 24 h. Solids were removed by suction filtration, and the filtrate was evaporated to dryness under reduced pressure. The residue was dissolved in 100 mL deionized water and extracted with $CH_2Cl_2$ three times. The organic phase was dried over $MgSO_4$ overnight, and the solvent was removed by rotary evaporation. The light yellow liquid product of HBBP was obtained in a yield of 69.5%. $^1$HNMR (300 MHz, $CDCl_3$): δ 1.90 (—CH($CH_3$)Br), 5.22 (—$CH_2$—OCO—), 4.73 (HO—$CH_2$—), 4.40 (CH($CH_3$)Br), 2.06 (HO—$CH_2$—), 7.40 ($CH_2$—$C_6H_4$—$CH_2$). Anal. Calcd (wt %) for $C_{11}H_{13}O_3Br$: C, 48.35; H, 4.76; O, 17.59; Br, 29.30. Found: C, 48.39; H, 4.68; O, 17.42; Br, 29.51.

Example 2

Synthesis of 2-Hydroxyethyl-2'-Bromopropionate (HEBP)

A 500-mL round-bottomed flask was charged with 62.0 g (1.00 mol) of ethylene glycol, 16.0 mL (0.114 mol) TEA, and 200 mL anhydrous THF. The solution was cooled to 0° C. and a solution of 21.6 g (0.10 mol) of 2-bromopropionyl bromide dissolved in 20 mL anhydrous THF was added dropwise under nitrogen at 0° C. for 2 h. Then the reaction temperature was raised to 40° C. for 24 h. Solids were removed by suction filtration, and the filtrate was evaporated to dryness under reduced pressure. The residue was dissolved into 100 mL deionized water and extracted with $CH_2Cl_2$ three times. The organic phase was dried over $MgSO_4$ overnight and the solvent was removed by rotary evaporation. The colorless liquid product was collected by distillation under reduced pressure: Yield: 61.8%; $^1$HNMR (300 MHz, $CDCl_3$): δ 1.90 (CH($CH_3$)Br), 4.29 ($CH_2$—OCO—), 3.85 (HO—$CH_2$—), 4.53 (—CH($CH_3$)Br), 2.06 (HO—$CH_2$—).

Example 3

Synthesis of Herringbone GCNFs

GCNFs of herringbone structure were grown from a Fe/Cu growth-catalyst powder as reported in the literature [Chambers et al, *J Phys Chem B* 1998, 102, 2251]. The Fe/Cu catalyst with atomic ratio of 7:3 was prepared by co-precipitation of $Fe(NO_3)_3.9H_2O$ and $Cu(NO_3)_2.3H_2O$ with ammonium bicarbonate in water. The precipitate was dried at 110° C. overnight and grounded to a fine powder. The powder was weighed into a quartz boat placed in tube furnace and calcined in an air flow at 400° C. for 4 h. Then, a $H_2$/He (1:4) flow of 250 mL/min was applied to reduce the iron/copper oxide at 500° C. for 20 h. After further reduction of the catalyst at 600° C. for 2 h, ethylene was introduced to grow the GCNFs with the gas composition of $C_2H_4/H_2$/He (4:1:1) at 600° C. over 90 min. The GCNFs were cooled to room temperature under He protection.

Example 4

Oxidation and Acylation of GCNFs

Surface oxidization of as-prepared GCNFs was performed by heating as-prepared GCNFs in concentrated nitric acid at 140° C. for 4 h. The product was filtered and washed with deionized water until pH≈7. The surface-oxidized carbon nanofibers (GCNF-$CO_2H$) were dried in vacuo at room temperature for 2 days to remove residual water. Then, the GCNF-$CO_2H$ nanofibers were acylchlorinated by reaction with thionyl chloride at 70° C. for 24 h in the presence of a small amount of dimethylformamide (DMF). The mixture was cooled down and washed with anhydrous THF under nitrogen until the supernate was clear. The black solid product of GCNF-C(O)Cl was dried under a nitrogen flow at room temperature before further reaction.

Example 5

Preparation of HBBP-Immobilized GCNFs (GCNF-HBBP-Br)

A 100-mL round-bottomed flask was charged with 0.42 g GCNF-C(O)Cl, 8.47 g (31.1 mmol) HBBP and 0.03 g (0.29 mmol) TEA. The mixture was allowed to react at 75° C. under the protection of $N_2$ for 144 h. The black solid was washed with methanol several times to remove excess HBBP and TEA. The product was collected by filtration through a 0.2 μm Millipore Nylon membrane and dried in vacuum. Elemental analysis (wt %): C, 90.64; H, 0.74; 0, 6.09; Br, 0.92.

Example 6

Preparation of HEBP-Immobilized GCNFs (GCNF-HEBP-Br)

A 100 mL round-bottomed flask was charged with 0.98 g GCNF-C(O)Cl, 6.53 g HEBP and 0.047 g TEA. The mixture was allowed to react at 75° C. under the protection of $N_2$ for 96 h. The black solid was washed with methanol for several times to remove excess HEBP and TEA. The product was collected by filtration through a 0.2 μm Millipore Nylon membrane and dried in vacuum. Elemental analysis (wt %): C, 92.89; H, 0.45; 0, 5.98; N, 0.18; Br, 0.50.

Example 7

Synthesis of GCNF-poly(n-butyl acrylate) (GCNF-PBA)

For a typical polymerization, a 100-mL dried Schlenk flask was charged with 200 mg GCNF-HBBP-Br, 112 mg (0.78 mmol) CuBr, 162 μL (0.78 mmol) PMDETA, and 1.00 g (7.8 mmol) n-butyl acrylate. The reaction mixture was degassed by five freeze-pump-thaw cycles. The flask was put into a 70° C. oil bath, and the mixture was stirred for 116 h. The reaction was quenched by liquid nitrogen, and 30 mL THF was added to disperse the black solid. The product was filtered through a 0.2 μm Millipore Nylon membrane and washed with THF. The dispersion-filtration-wash process was repeated six times to ensure that no un-grafted polymers remained in the residue. Then the dark solid was dispersed in methanol followed by filtration to remove catalyst. The collected product was dried in vacuum at room temperature, resulting in 356 mg solid product.

Example 8

ATRP of nBA (PBA)

Control experiments for the polymerization of n-butyl acrylate initiated by HBBP were carried out in bulk to demonstrate the ATRP behavior of the system applied to the synthesis of GCNF-PBA. In a typical experiment, a dry 100 mL Schlenk flask was charged with 44.8 mg CuBr (0.31 mmol), 64.9 μL PMDETA (0.31 mmol), 85.2 mg HBBP (0.31 mmol), and 2.0 g n-butyl acrylate (15.6 mmol), and the mixture was degassed by three freeze-pump-thaw cycles. The flask was put into an oil bath at 70° C. After 2 h, the viscosity of the mixture increased dramatically, and the polymerization reaction was quenched by liquid nitrogen. The mixture was dissolved in 30 mL THF and passed through an alumina column to remove the catalyst. THF was removed by rotary evaporation under reduced pressure, and the polymer product was dried in vacuum at 50° C. for 16 h. Specific reaction conditions and polymer yields for these control polymerizations are provided in Table 1.

TABLE 1

Conditions and results of ATRP of nBA initiated by HBBP.*

| Sample | [nBA]:[CuBr]:[PMDETA]:[HBBP] | Time (h) | Mn | Mw/Mn | Yield (%) |
|---|---|---|---|---|---|
| PBA0[a] | 50:1:1:1 | 2 | 5.300 | 1.20 | 99.1 |
| PBA0[a] | 50:1:1:1 | 2 | 5.300 | 1.20 | 99.1 |
| PBA1[b] | 50:1:1:1 | 2 | 4.900 | 1.49 | 58.5 |
| PBA2[c] | 50:1:1:1 | 20 | 7.300 | 1.31 | 98.6 |

[a]Reaction temperature of 70° C.,
[b]In the presence of as-prepared GCNFs, [BA]:[GCNFs] = 10:1 (wt/wt),
[c]In the presence of GCNF-COOH, [BA]:[GCNF-COOH] = 10:1 (wt/wt).

Example 9

ATRP Control Experiments c-GCNF or c-GCNF—$CO_2H$

Control experiments for the polymerization of monomer in the presence of as-prepared GCNFs or oxidized GCNFs, GCNF-$CO_2H$ were performed for each monomer, respectively. Experimental conditions were the same as that of the ATRP of pure monomer except that as-prepared GCNFs or oxidized GCNFs were present in a monomer/GCNF additive ratio of 10:1 wt/wt. The product was purified by dispersing the resulting mixture into 30 mL THF, filtering the obtained suspension through a 0.2 μm Millipore Nylon membrane, and washing the collected residue with excess THF. The dispersion-filtration-wash process was repeated six times. The filtrate was rotary evaporated to near dryness, and the polymer product was dried in vacuum at 50° C. for 16 h. The residue was washed with MeOH three times and dried in vacuum at room temperature for 16 h.

Example 10

Cleavage of poly(n-butyl acrylate) from GCNF-PBA

A representative cleavage reaction was performed by dispersing 0.1602 g GCNF-PBA3 into 100 mL toluene followed by adding 100 mL n-butanol and 5 mL concentrated sulfuric acid and refluxing the mixture at 100° C. for 9 days. The solvent was removed by rotary evaporation. The residual solid was dispersed into 100 mL $CHCl_3$ and extracted with water three times to remove sulfuric acid. The organic dispersion was filtered through a 0.2 μmMillipore Nylon membrane and washed with $CHCl_3$. The filtrate was rotary evaporated to remove solvent and dried in vacuum overnight at 50° C. Molecular weight and polydispersity of the cleaved PBA were measured by GPC-MALLS; Mw=31,300, Mw/Mn=1.73.

Example 11

Synthesis of GCNF-poly(iso-butyl methacrylate) (GCNF-PiBMA)

For a typical polymerization a 25-mL dried round-bottom flask was charged with 0.20 g GCNF-HEBP-Br and 12.3 mg (0.124 mmol) CuCl. The flask was sealed with a rubber septum and degassed and refilled with nitrogen three times. Deoxygenated acetone (4 mL) was added into the flask followed by the addition of 26 μL (0.124 mmol) PMDETA via syringe. The mixture was sonicated for 15 min to form a uniform dispersion. After the addition of 4 mL (24.7 mmol) deoxygenated iso-butyl methacrylate via syringe, the flask was put into a 50° C. oil bath for 96 h. The reaction was quenched by liquid nitrogen, and THF was added to disperse the black solids. The product was filtered through a 0.2 μm Millipore Nylon membrane and washed with THF. The dispersion-filtration-wash process was repeated six times to ensure no un-grafted polymers remained in the residue. Then the dark solids were dispersed in methanol and filtered to remove the catalyst. The collected product was dried in vacuum at room temperature.

Example 12

ATRP of iso-BMA in the Presence of GCNF-$CO_2H$ (GCNF-$CO_2H$/PiBMA)

A 25-mL dried round-bottom flask was charged with 0.20 g GCNF-$CO_2H$ and 12.3 mg (0.124 mmol) CuCl. The flask was sealed with a rubber septum and degassed and refilled with nitrogen three times. Deoxygenated acetone (4 mL) was added into the flask followed by the addition of 26 μL (0.124 mmol) PMDETA via syringe. The mixture was sonicated for 15 min to form a fine dispersion. Then 4 mL (24.7 mmol) deoxygenated iso-butyl methacrylate was added into the flask via syringe, and the mixture was stirred for 5 min. Finally, 30 μL (0.247 mmol) HEBP was added via syringe, and the flask was put into a 50° C. oil bath for 20 h. The reaction was quenched by liquid nitrogen, and THF was added to disperse the black solid. The product was filtered through a 0.2 μm Millipore Nylon membrane and washed with THF. The filtrate was passed through an alumina column to remove catalyst, and the solvent was removed by rotary evaporation. The polymer product was dried under reduced pressure at 50° C. for 16 h. The solid residue was purified by repeated dispersion-filtration-THF washing (four times) to remove non-grafted polymers. The collected solid was dried in vacuum at room temperature for 16 h.

Example 13

ATRP of iso-BMA (PiBMA)

A 25-mL, dried round-bottom flask was charged with 12.3 mg (0.124 mmol) CuCl. The flask was sealed with a rubber septum and degassed and refilled with nitrogen three times. Deoxygenated acetone (4 mL) was added into the flask followed by the addition of 26 µL (0.124 mmol) PMDETA via syringe. The mixture was sonicated for 15 min to form an even dispersion. Then 4 mL (24.7 mmol) deoxygenated iso-butyl methacrylate was added into the flask via syringe, and the mixture was stirred for 5 min. Finally, 30 µL (0.247 mmol) HEBP was added via syringe, and the flask was put into a 50° C. oil bath for 20 h. The reaction was quenched by liquid nitrogen, and THF was added to dilute the mixture. Catalyst was removed by passing the solution through an alumina column, and the solvent was removed by rotary evaporation. The polymer product was dried in vacuum at 50° C. for 16 h.

Example 14

Synthesis of GCNF-poly(tert-butyl acrylate) (GCNF-PtBA)

A 25-mL dried round-bottom flask was charged with 0.20 g GCNF-HEBP-Br and 38.7 mg (0.27 mmol) CuBr. The flask was sealed with a rubber septum and degassed and refilled with nitrogen three times. Deoxygenated acetone (4 mL) was added into the flask followed by the addition of 56.6 µL (0.27 mmol) PMDETA via syringe. The mixture was sonicated for 15 min to form an even dispersion. After the addition of 4 mL (27 mmol) deoxygenated tert-butyl acrylate via syringe, the flask was put into a 60° C. oil bath for 22 h. The purification process of the product was the same as that of GCNF-PiBMA.

Example 15

ATRP of tBA in the Presence of GCNF-$CO_2$H (GCNF-$CO_2$H/PtBA)

A 25-mL dried round-bottom flask was charged with 0.20 g GCNF-$CO_2$H and 38.7 mg (0.27 mmol) CuBr. The flask was sealed with a rubber septum and degassed and refilled with nitrogen three times. Deoxygenated acetone (4 mL) was added into the flask followed by the addition of 56.6 µL (0.27 mmol) PMDETA via syringe. The mixture was sonicated for 15 min to form an even dispersion. Then 4 mL (27 mmol) deoxygenated tert-butyl acrylate was added into the flask via syringe, and the mixture was stirred for 5 min. Finally, 30 µL (0.27 mmol) MBrP was added via syringe, and the flask was put into a 60° C. oil bath for 22 h. The purification process of the product was the same as that of GCNF-$CO_2$H/PiBMA.

Example 16

ATRP of tBA (PtBA)

A 25-mL dried round-bottom flask was charged with 38.7 mg (0.27 mmol) CuBr. The flask was sealed with a rubber septum and degassed and refilled with nitrogen three times. Deoxygenated acetone (4 mL) was added into the flask followed by the addition of 56.6 µL (0.27 mmol) PMDETA via syringe. Then 4 mL (27 mmol) deoxygenated iso-butyl acrylate were added into the flask via syringe, and the mixture was stirred for 5 min. Finally, 30 µL (0.27 mmol) MBrP was added via syringe, and the flask was put into a 60° C. oil bath for 22 h. The reaction was quenched by liquid nitrogen, and acetone was added to dilute the mixture. Catalyst was removed by passing the solution through an alumina column, and the solvent was evaporated by rotary evaporation. The polymer product was dried in vacuum at 50° C. for 16 h.

Example 17

Preparation of GCNF-Poly(Acrylic Acid) (GCNF-PAA)

Hydrophilic GCNF/poly(acrylic acid) brushes were obtained by acid hydrolysis of PtBA chains of the GCNF-PtBA sample. Typically, 50 mg of GCNF-PtBA was dispersed into 15 mL $CHCl_3$ in a 25 mL flask and 2.5 mL $CF_3CO_2H$ was added thereafter. The mixture was stirred at room temperature for 24 h under nitrogen protection. The reaction mixture was rotary evaporated under vacuum to remove the reagents, and the black powder of GCNF-PAA product was collected for further characterization. As described above, herringbone GCNFs of ca. 150 nm average diameter were prepared in multi-gram quantities at 600° C. using a 7:3 Fe/Cu growth catalyst and flowing $C_2H_4/H_2$/He (4:1:1) as the carbonaceous gas following established procedures. Oxidation of GCNF surface sites by nitric acid followed by sequential reaction with thionyl chloride and either HBBP or HEBP gives GCNFs containing surface-bound ATRP radical initiators, GCNF-HBBP-Br or GCNF-HEBP-Br (see Scheme 1 in FIG. 1).

The structural integrity of the GCNFs is maintained throughout surface derivatization. The polymerization of acrylate monomers occurs at elevated temperature in the presence of GCNF-HBBP-Br or GCNF-HEBP-Br and CuCl or CuBr/PMDETA (N,N,N',N'',N''-pentamethyldiethylenetriamine) as catalyst. Representative reaction conditions are provided in Table 2 for several GCNF-PBA polymer brush syntheses (including polymer content).

TABLE 2

Typical Reaction Conditions and Polymer Content

| Brush 1a | [nBA]:[I][a] | Catalyst Ratio[b] | T (° C.) | t (h) | PBA wt %[c] |
|---|---|---|---|---|---|
| GCNF-PBA1 | 3400:1 | 200:1:1 | 70 | 168 | 11 |
| GCNF-PBA2 | 3400:1 | 10:1:1 | 70 | 96 | 17 |
| GCNF-PBA3 | 340:1 | 10:1:1 | 70 | 116 | 34 |
| GCNF-PBA4 | 750:1 | 10:1:1 | 70 | 263 | 35 |

[a]Molarity of immobilized initiator calculated by (wt GCNF-HBBP-Br × 0.115 mmol/g).
[b]Catalyst ratio = [nBA]:[CuBr]:[PMDETA].
[c]Obtained from TGA analysis.

ATRP control reactions of (1) free initiator with monomer, (2) free initiator with monomer in the presence of as-prepared GCNFs, and, (3) free initiator with monomer in the presence of GCNF-$CO_2$H indicate significant radical trapping by the presence of free carbon nanofibers. In polymerizations of 2 h duration, polymer yield is reduced by ca. 40% in the presence of as-prepared GCNFs. In the presence of GCNF-$CO_2$H, a 20-h reaction time is required to achieve polymer yields comparable to those obtained from free monomer and free initiator syntheses.

Figures 2A, 2B:
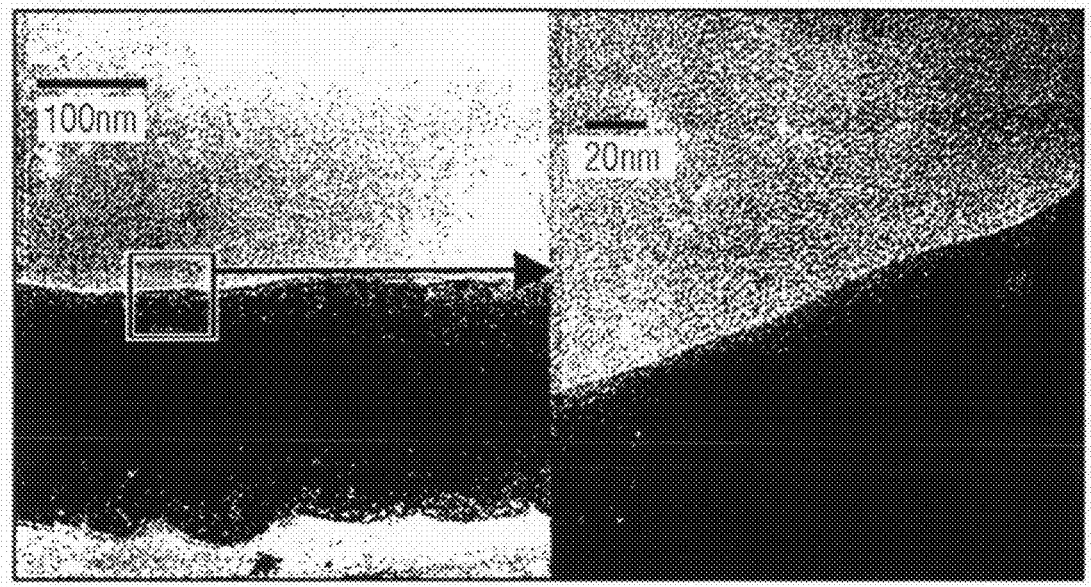
FIGS. 2A-2B are TEM micrographs of the GCNF-PBA brush, 1a, at two different magnifications.

TEM micrographs representative of GCNF/polymer brushes are shown in FIGS. 2A-2B for polymer brush 1a. A continuous polymer brush layer of 20-50 nm thickness is observed. ATRP probably occurs at various relative rates due to disparate local reaction conditions affording polymer brush layers of non-uniform thickness. When cleaved from the nanofiber surface and analyzed by GPC-MALLS, the polymer brush of 1a (GCNF-PBA4) has a weight average molecular weight (Mw) of 31,000 with a polydispersity of 10.73. A polydispersity of this magnitude is consistent with diverse growth rates of individual polymer chains due to local-site heterogeneity. MWNT-PS brushes, also prepared via surface-initiated ATRP, exhibit large polydispersity (3.08) for similar reasons [Ros et al, *Chem. Eur. J.* 2002, 8, 1151].

Figure 3:
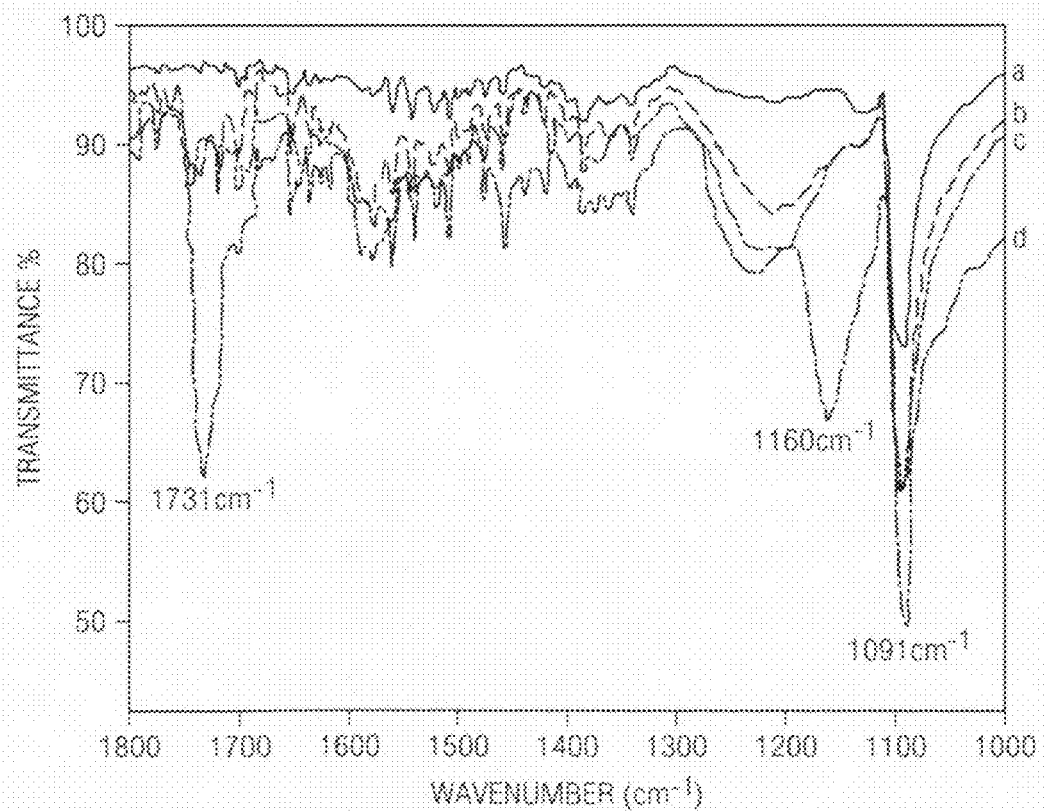
FIG. 3 illustrates an FT-IR spectra of (a) GCNFs, (b) GCNF-HBBP-Br, (c) GCNF-COOH and (d) GCNF-PBaA4.

Representative changes in FT-IR spectral data for a related series of GCNF materials are shown in FIG. 3. As-prepared GCNFs exhibit a strong C—C stretching band near 1091 $cm^{-1}$ and weak bands near 1580 $cm^{-1}$ assigned to graphene sheet vibrations. Surface-oxidized GCNFs, GCNF-$CO_2H$, show carbonyl C=O stretching bands at 1716 $cm^{-1}$ and 1731 $cm^{-1}$ with increased band intensity near 1217 $cm^{-1}$ due to the presence of C—O stretching and C—O—H bending vibrations. Covalent attachment of HBBP initiator groups to surface $CO_2H$ sites using esterification chemistry causes few distinctive changes in the FT-IR spectrum. However, growth of the corresponding poly(acrylate) chains is evidenced by the appearance of strong bands characteristic of polymer functional groups. Spectra of polymer brushes 1a, 2a, and 2b show strong bands at 1731 $cm^{-1}$ and 1160 $cm^{-1}$ associated with C—O and C=O stretching bands of ester functional groups, while the carbonyl C=O stretching band shifts to ca. 1575 $cm^{-1}$ for the GCNF-(poly-acrylic acid) brush, 2c.

Figure 4:
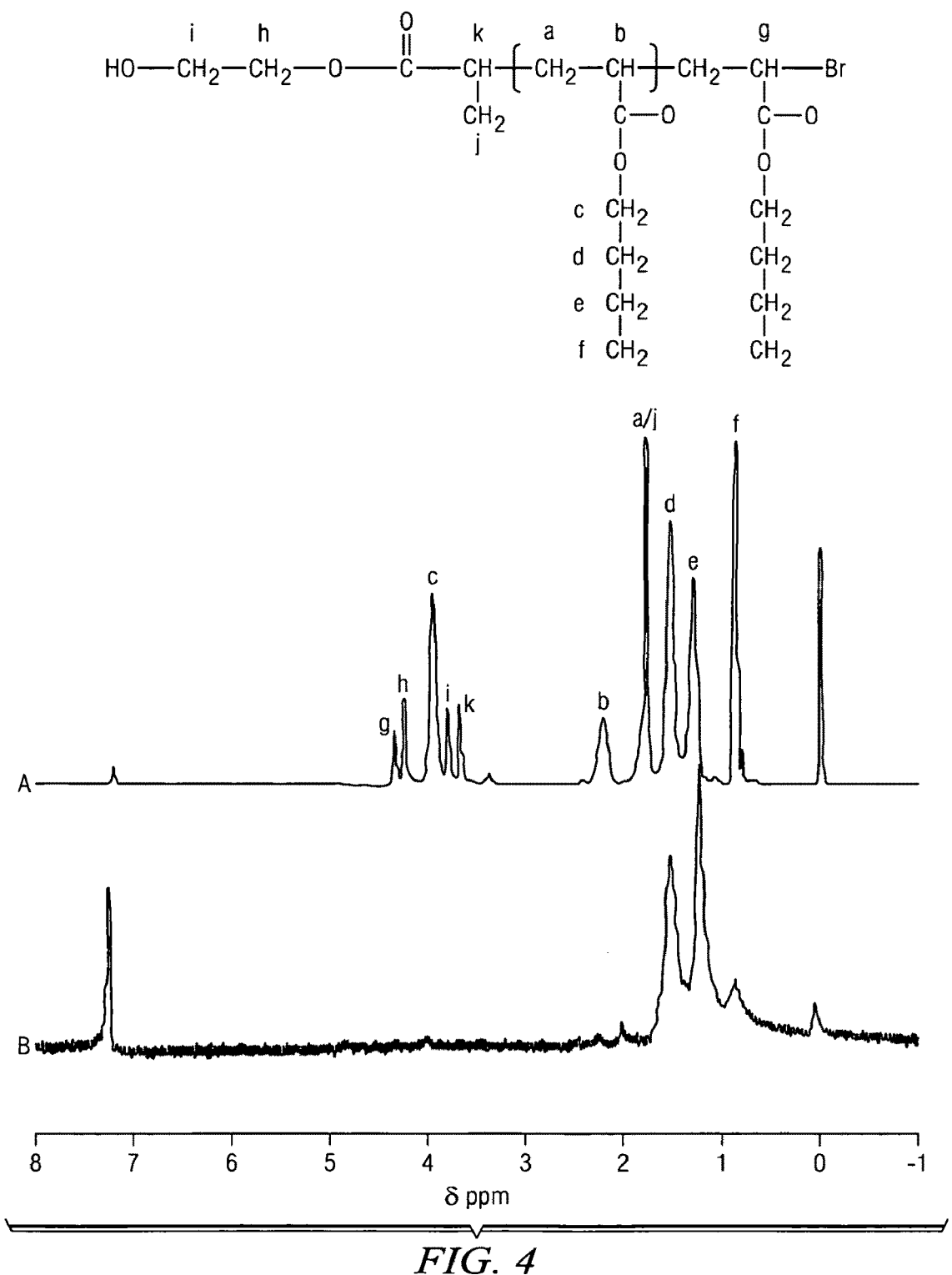
FIG. 4 illustrates an H-NMR spectra of (A) PBA, (B) GCNF-PBA3 in $CDCl_3$.

$^1$HNMR spectra of PBA and of GCNF/polymer brush, GCNF-PBA3 (see FIG. 4) are consistent with the presence of surface-bound poly(n-butyl acrylate) chains in this GCNF/polymer brush material. Resonances at 0.91 ppm, 1.34 ppm, and 1.58 ppm are assigned, respectively, to the n-butyl methyl and methylene groups within the poly(n-butyl acrylate) chains. Compared to the corresponding resonance intensities of PBA, the intensities of backbone proton resonances of the polymer brush are dramatically reduced due to relaxation broadening resulting from restricted motion. This phenomenon, which is related to the solid-like properties of surface-bounded polymers, has been observed for related polymer brush materials and is expected for GCNF/polymer brushes, as well [Blum, F. D. *Annu. Rep. NMR Spectrosc.* 1994, 28, 277].

Figure 5:
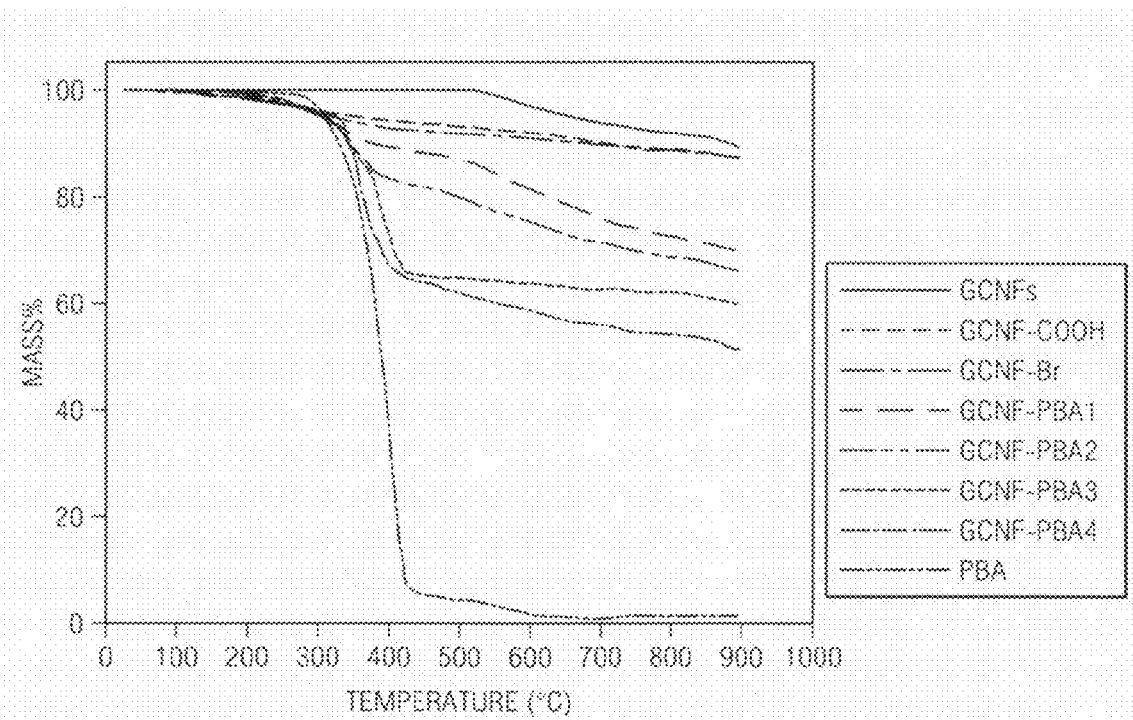
FIG. 5 illustrates TGA traces of as-prepared GCNFs, oxidized GCNFs (GCNF-COOH), initiator-immobilized GCNFs (GCNF-Br 1), GCNF/PBA brushes (GCNF-PBA1-GCNFPBA4), and pure poly(n-butyl acrylate) where TGA analysis was carried out under a nitrogen gas atmosphere to avoid air oxidation.

TGA mass-loss curves of a family of GCNF/polymer brushes 1a (GCNF-PBA 1-GCNF-PBA4) and related intermediate materials are shown in FIG. 5. For as-prepared GCNFs, mass loss onset occurs at 570° C. due to the excellent thermal stability of stacked graphene sheets. The 10.6 wt % mass loss from 570° C. to 900° C. is attributed to decomposition of randomly oxidized surface defect sites, probably as $CO/CO_2$ [Ros, et al. *Chem. Eur. J.* 2002, 8, 1151]. Oxidized GCNFs contain a variety of oxidized carbon species with a predominance of $CO_2H$ functional groups. Gradual mass loss from 150° C.-900° C. is assigned to CO and $CO_2$ evolution from a variety of oxygen-containing surface functional groups. Mass loss curves for surface-bound profiles similar to that of oxidized GCNFs due to the small absolute mass incorporated as initiator molecules.

However, thermal decomposition of GCNF-PBA polymer brush materials occur as very evident single, mass loss events centered near 400° C. This event parallels that observed for pure PBA and is associated with the presence of surface-bound PBA polymer chains. The corresponding PtBA polymer brush, 2b, thermally decomposes as two mass-loss events that also parallel those observed for pure PtBA (see Supporting Information). Sharp mass loss centered at ca. 215° C. is assigned to degradation of tBu groups, while a broad mass loss at ca. 385° C. is consistent with decarboxylation of ester functional groups.

Figure 6:
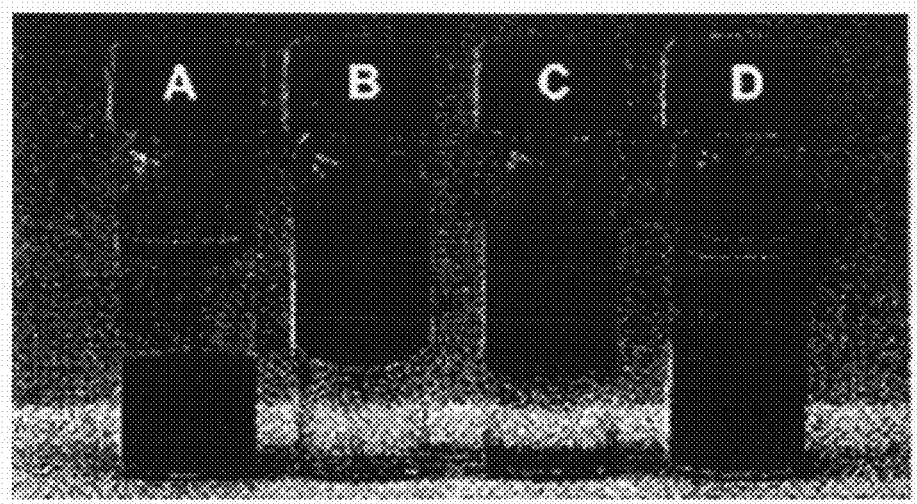
FIG. 6 illustrates dispersibilities of the hydrophobic GCNF-PBA brush, 1a, in water (upper)/$CHCl_3$(lower) vial A, and in toluene(upper)/CHCl3(lower), vial B, contrasted with that of the hydrophilic GCNF-PAA brush, 2c, in water(upper)/$CHCl_3$(lower), vial C, and in toluene(upper)/water (lower), vial D; where GCNF-polymer brush concentration are ca. 2 mg/mL.

Acid hydrolysis of polymer brush 2b affords polymer brush 2c containing carboxylic acid groups within each repeat unit. As shown in FIG. 6, the solution dispersibility of GCNF-polymer brushes is controlled by the solubility properties of the polymer phase. Polymer brushes containing ester functional groups, such as the GCNF-PBA brush, 1a, are hydrophobic, while polymer brush 2c containing carboxylic acid groups is hydrophilic. GCNF-PtBA polymer brushes form stable dispersions in $CHCl_3$ and toluene but not in water (see Supporting Information for additional dispersibility data).

From the BET surface area of oxidized GCNFs (26 $m^2/g$), which best represents GCNF after oxidative etching and knowing the polymer content and average molecular weight of GCNF-PBA polymer brushes, an average surface density of polymer brush chains is calculated to be ca. 3 polymer chains/10 $nm^2$. Since an ideal stacking pattern of graphene sheets contains ca. 120 unsaturated edge carbon atoms/10 $nm^2$, ca. 1 of every 40 GCNF surface edge sites is functionalized with a polymer chain. This relatively high surface functionalization accounts for the solution dispersibility properties imparted to graphitic carbon nanofibers through polymer brush formation.

The present invention demonstrates that, by using surface derivatization chemistry, as-prepared GCNFs can be functionalized with ATRP initiators. Polymerization in the presence of acrylate or methacrylate ester monomers affords hydrophobic and, through ester hydrolysis, hydrophilic GCNF-polymer brush materials. By controlling both polymer brush functional group reactivity and dispersibility properties, a wide range of GCNF/polymer brush hybrid composite materials are now accessible. In other configurations, such materials could potentially function as analyte-selective sensors for chemical- or bio-agent detection.

Elemental analysis data; reaction conditions; TEM and AFM images; FT-IR spectra; TGA curves; dispersibility data; BET surface area analysis data; and GPC trace. This material, the entire contents and disclosure of which is incorporated herein by reference, is available via the Internet at http://pubs.acs.org. erringbone In summary, herringbone, as well as other, rushes are prepared by atom-transfer-radical-polymerization (ATRP) using the "grafted-from" synthesis strategy. Initiated polymerization of (meth)acrylate monomers at GCNF surface sites affords hydrophobic GCNF/poly(n-butyl acrylate), GCNF/poly(iso-butyl methacrylate), and GCNF/poly(tert-butyl acrylate) polymer brushes. Acid hydrolysis of the GCNF/poly(tert-butyl acrylate) polymer brush gives a hydrophilic GCNF/poly(acrylic acid) polymer brush. The average surface density of the polymer brush chains is ca. 3 polymer chains/10 $nm^2$.

Synthesis of GCNF/Polymer Brushes Via Atom Transfer Radical Polymerization

Herringbone GCNFs possess canted graphite sheets stacked in a nested fashion along the long fiber axis. GCNFs of this type can be prepared by catalytic CVD of carboneous gases at elevated temperature having average diameters from 25 nm-200 nm and lengths on the micron scale. The graphitic atomic structure of herringbone GCNFs gives a carbon nanofiber long-axis surface comprised of C(sp$^2$) edge sites, usually passivated by hydrogen atoms. Refluxing as-prepared herringbone GCNFs in concentrated nitric acid not only removes metallic catalyst particles and amorphous carbon impurities but oxidizes C atoms at the edge sites of graphene sheets. Surface-functionalization of herringbone GCNFs with reactive linker molecules using surface oxidation and carboxyl group coupling chemistry occurs without degradation of the structural integrity of the GCNF backbone and affords surface-derivatized GCNFs having a high surface density of functional groups. Covalent binding of such linker molecules to either polymer resins or ceramic condensation oligomers gives GCNF/polymer or GCNF/ceramic hybrid materials. An even greater complexity of functional group derivatization could be achieved by grafting organic polymers to GCNF surface sites to give GCNF/polymer brushes having tunable dispersibilities and surface reactivity. Proven by the synthesis of hydrophobic and hydrophilic CNT/polymer brushes, surface-initiated ATRP of (meth)acrylate monomers is a preferable method for growing polymer brushes from the surface of GCNFs.

The invention can include the synthesis of herringbone GCNF/polymer brushes of GCNF-poly(n-butyl acrylate), GCNF-PBA, GCNF-poly(iso-butyl methacrylate), GCNF-PiBMA, GCNF-poly(tert-butyl acrylate), GCNF-PtBA, GCNF-poly(glycidyl methacrylate), GCNF-PGMA, and GCNF-poly(acrylic acid), GCNF-PAA by in situ ATRP using a "grafted from" approach. While GCNF-poly(meth)acrylate polymer brushes exhibit hydrophobic dispersibility, the GCNF-PAA brush is hydrophilic. The invention can include a synthesis strategy amenable to the preparation of a wide variety of GCNF/polymer materials.

Materials

Gaseous ethylene, hydrogen and helium were procured from Air Liquide Gas. 1,4-benzenedimethanol (97%), ethylene glycol (99.8%), 2-bromopropionyl bromide (97%), 2,2,2-trichloroethanol (TCE, 98%), methyl 2-bromopropionate (MBrP, 98%), CuBr (99.999%), CuCl (99.999%), N,N,N',N",N"-pentamethyldiethylenetriamine (PMDETA, 99%), 4-dimethylaminopyridine (DMAP, 99%), and triethylamine (TEA, 99.5%) were purchased from Aldrich and used as received. n-Butyl acrylate (BA, Aldrich, 99%), iso-butyl methacrylate (iBMA, Aldrich, 99%), tert-butyl acrylate (tBA, Aldrich, 98%) and glycidyl methacrylate (GMA, Aldrich, 97%) were purified by passing through an alumina column and stored under N$_2$ at −15° C. for use. Solvents were distilled before use and other reagents were used without further purification.

Instruments and Measurements

Transmission electron microscopy (TEM) was performed on a Philips CM-20T Electron Microscope operated at 200 KeV. 300 MHz $^1$H-NMR spectra were recorded on a Bruker AC300 Fourier transform spectrometer, using CDCl$_3$ as solvent. Infrared spectra (IR) were obtained from KBr pressed pellets with an ATI Mattson Genesis Series FT-IR spectrometer. Thermogravimetric analyses (TGA) were performed on a Thermal Analysis Instruments High-Resolution TGA 2950 Thermogravimetric Analyzer. Elemental analysis was performed by Atlantic Microlab, Inc., Norcross, Ga. BET surface area analysis was carried out on a NOVA 1000 High Speed Surface Area & Pore Size Analyzer using nitrogen gas as the absorbent.

Synthesis of (4-Hydroxymethyl)-Benzyl 2-Bromopropionate (HBBP)

A 500-mL round-bottomed flask was charged with 13.06 g (94.5 mmol) 1,4-benzenedimethanol, 20 mL (0.145 mol) TEA, 0.24 g (2.0 mmol) DMAP and 200 mL anhydrous THF. The solution was cool down to 0° C. and a solution of 10 mL (94.5 mmol) 2-bromopropionyl bromide dissolved into 20 mL anhydrous THF was added dropwise under nitrogen at 0° C. for 2 h. Then the reaction mixture was raised to 40° C. and stirred for 24 h. Solids were removed by suction filtration, and the solvent of THF was evaporated under reduced pressure. The remaining solids were dissolved into 100 mL deionized water and extracted with CH$_2$Cl$_2$ for three times. The organic phase was dried over MgSO$_4$ overnight, and the solvent was removed by rotary evaporation. The light yellow liquid product of HBBP gave the yield of 69.5%. $^1$H-NMR (300 MHz, CDCl$_3$): δ=1.90 (—CH(CH$_3$)Br), δ=4.22 (—CH$_2$—OCO—), δ=4.40 (HO—CH$_2$—), δ=4.73 (—CH(CH$_3$)Br), δ=5.22 (HO—CH$_2$—), δ=7.40 (—CH$_2$—C$_6$H$_4$—CH$_2$—).

Synthesis of 2-Hydroxyethyl-2'-Bromopropionate (HEBP)

A 500-mL round-bottomed flask was charged with 62.0 g (1.00 mol) ethylene glycol, 16.0 mL (0.114 mol) TEA, and 200 mL anhydrous THF. The solution was cool down to 0° C., and a solution of 21.6 g (0.10 mol) 2-bromopropionyl bromide dissolved into 20 mL anhydrous THF was added dropwise under nitrogen at 0° C. for 2 h. Then the reaction temperature was raised to 40° C. for 24 h. Solids were removed by suction filtration, and the solvent was removed under reduced pressure. The remaining solids were dissolved into 100 mL deionized water and extracted with CH$_2$Cl$_2$ three times. The organic phase was dried over MgSO$_4$ overnight, and the solvent was removed by rotary evaporation. The colorless liquid product was collected by distillation under reduced pressure. Yield: 61.8%. $^1$H-NMR (300 MHz, CDCl$_3$): δ=1.90 (—CH(CH$_3$)Br), δ=4.29 (—CH$_2$—OCO—), δ=3.85 (HO—CH$_2$—), δ=4.53 (—CH(CH$_3$)Br), δ=2.06 (HO—CH$_2$—).

Synthesis of Herringbone GCNFs

The GCNFs with herringbone structure were grown from the Fe/Cu catalyst powder as reported elsewhere. The Fe/Cu catalyst with atomic ratio of 7:3 was prepared by co-precipitation of Fe(NO$_3$)$_3$.9H$_2$O and Cu(NO$_3$)$_2$.3H$_2$O with ammonium bicarbonate in water. The precipitate was dried at 110° C. overnight and grounded to fine powder. The powder was weighed into a quartz boat placed in a tubular furnace and calcined in an air flow at 400° C. for 4 h. Then a H$_2$/He (1:4) flow of 250 mL/min was applied to reduce the iron/copper oxide at 500° C. for 20 h. After further reduction of the catalyst at 600° C. for 2 h, ethylene was introduced to grow GCNFs with a gas composition of C$_2$H$_4$/H$_2$/He (4:1:1) at 600° C. for 90 min. Obtained GCNFs were cooled to room temperature under He protection.

Oxidation and Acylation of GCNFs

Surface oxidization of as-prepared GCNFs was performed in concentrated nitric acid at 140° C. for 4 h. The product was filtrated and washed with deionized water until pH≈7. The surface-oxidized carbon nanofibers (GCNF-CO$_2$H) were dried in vacuum at room temperature for 2 days to remove residual water. Then GCNF-CO$_2$H nanofibers were reacted with thionyl chloride at 70° C. for 24 h in the presence of a small amount of dimethylformamide (DMF). The mixture was cooled down and washed with anhydrous THF under nitrogen until the supernatant liquid was clear. The black solid product of GCNF-C(O)Cl was dried with nitrogen flow at room temperature for further reaction.

Preparation of HBBP-Immobilized GCNFs (GCNF-HBBP-Br)

A 100-mL round-bottomed flask was charged with 0.42 g GCNF-C(O)Cl, 8.47 g (31.1 mmol) HBBP and 0.03 g (0.29 mmol) TEA. The mixture was allowed to react at 75° C. under $N_2$ protection for 144 h. The black solids were washed with methanol for several times to remove excess HBBP and TEA. The product of GCNF-HBBP-Br was collected after filtration through a 0.2 µm Millipore PC membrane and dried in vacuum at room temperature.

Preparation of HEBP-Immobilized GCNFs (GCNF-HEBP-Br)

A 100-mL round-bottomed flask was charged with 0.98 g GCNF-C(O)Cl, 6.53 g HEBP and 0.047 g TEA. The mixture was allowed to react at 75° C. under the protection of $N_2$ for 96 h. Purification process was the same as that of GCNF-HBBP-Br.

Preparation of TCE-Immobilized GCNFs (GCNF-Cl)

A 250-mL Schlenk flask was charged with 4.0 g GCNF-C(O)Cl, 20 mL TCE and 20 mL anhydrous THF, followed by adding 0.2 mL TEA. Under $N_2$ protection, the flask was set up with a dry condenser and put into 75° C. oil bath for 48 h. The reaction mixture was filtered through a 0.45 µm Nylon membrane, washed with methanol 4 times, and then the GCNF-Cl product was vacuum dried at room temperature overnight.

Synthesis of GCNF-Poly(n-Butyl Acrylate) (GCNF-PBA)

Figure 7:
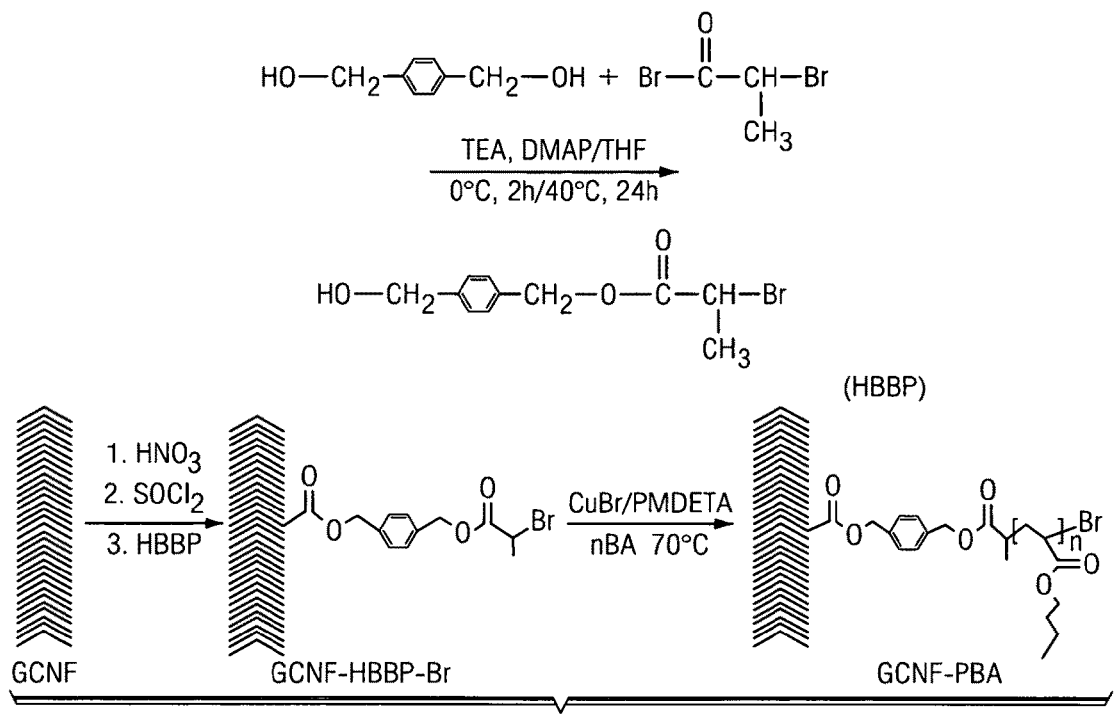
FIG. 7 illustrates a process strategy for synthesis of PBA brushes on the surface of herringbone GCNFs.

FIG. 7 shows a strategy for synthesis of PBA brushes on the surface of herringbone GCNFs. For a typical polymerization: a 100-mL dried Schlenk flask was charged with 200 mg GCNF-HBBP-Br, 112 mg (0.78 mmol) CuBr, 162 µL (0.78 mmol) PMDETA, and 1.00 g (7.8 mmol) n-butyl acrylate. The reaction mixture was degassed by five freeze-pump-thaw cycles. The flask was put into a 70° C. oil bath, and the mixture was kept stirring for 116 h. The reaction was quenched by liquid nitrogen, and 30 mL THF was added to disperse the black solid. The product was filtered through a 0.2 µm Nylon membrane and washed with THF. The dispersion-filtration-wash process was repeated six times to ensure no un-grafted polymers left in the residue. Then the dark solid was dispersed in methanol followed by filtration to remove catalyst reagents. The collected product was dried in vacuum at room temperature, resulting in 356 mg solid product.

ATRP of n-BA in the Presence of GCNF-$CO_2$H

The polymerization conditions were the same as that of the ATRP of n-butyl acrylate described above except that as-prepared GCNFs were added at the ratio of n-butyl acrylate:GCNFs=10:1 wt/wt. The product was purified by dispersing the resulting mixture into 30 mL THF, filtrating through a 0.2 µm Nylon membrane, and washing with excess THF. The dispersion-filtration-wash process with THF was repeated six times. The filtrate was distilled under reduced pressure and dried in vacuum at 50° C. overnight. The residual solid was washed with MeOH three times and dried in vacuum at room temperature overnight.

ATRP of n-BA

Control experiments of n-butyl acrylate polymerization initiated by HBBP were carried out in bulk to establish a synthesis protocol for the preparation of GCNF-PBA polymer brushes. In a typical experiment, a dry 100-mL Schlenk flask was charged with 44.8 mg CuBr (0.31 mmol), 64.9 PMDETA (0.31 mmol), 85.2 mg HBBP (0.31 mmol), and 2.0 g n-butyl acrylate (15.6 mmol). The mixture was degassed by three freeze-pump-thaw cycles, and the flask was put into an oil bath at 70° C. for 2 h. The mixture was quenched by liquid nitrogen and then dissolved in 30 mL THF. The solution was passed through an alumina column to remove catalyst molecules. Solvent was removed by rotary evaporation under reduced pressure and the viscous liquid product of PBA was dried in vacuum at 50° C. overnight.

Cleavage of Poly (n-Butyl Acrylate) from GCNF-PBA

A typical cleavage reaction was performed by dispersing 0.1602 g GCNF-PBA3 into 100 mL toluene followed by adding 100 mL n-butanol and 5 mL concentrated sulfuric acid and refluxing the mixture at 100° C. for 9 days. Solvent was removed by rotary evaporation under reduced pressure. The residual solid was dispersed into 100 mL $CHCl_3$ and extracted with water three times to remove any sulfuric acid. The organic dispersion was filtered through a 0.2 µm Nylon membrane and washed with $CHCl_3$. The filtrate was distilled under reduced pressure to remove the solvent and dried in vacuum overnight at 40° C. Molecular weight and polydispersity of the cleaved PBA were measured by GPC. (Mw=31,300, Mw/Mn=1.73)

Synthesis of GCNF-Poly(iso-Butyl Methacrylate) (GCNF-PiBMA)

Figure 8:
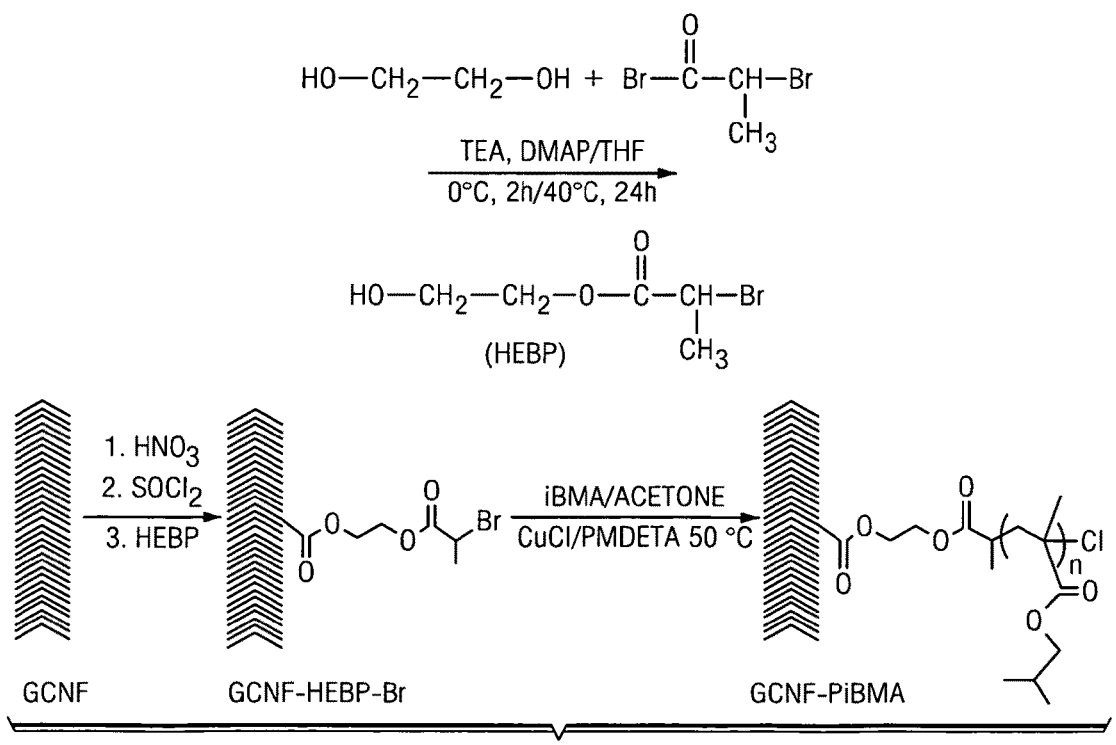
FIG. 8 illustrates a process strategy for synthesis of PiBMA brushes on the surface of herringbone GCNFs.

FIG. 8 shows a strategy for synthesis of PiBMA brushes on the surface of herringbone GCNFs. For a typical polymerization: a 25-mL dried round-bottom flask was charged with 0.20 g GCNF-HEBP-Br and 12.3 mg (0.124 mmol) CuCl. The flask was sealed with a rubber septum and degassed and refilled with nitrogen for three times. Deoxygenated acetone (4 mL) was added into the flask followed by the addition of 26 µL (0.124 mmol) PMDETA via syringe. The mixture was stirred for 10 min to form the Cu complex. After the addition of 4 mL (24.7 mmol) deoxygenated iso-butyl methacrylate via syringe, the flask was put into a 50° C. oil bath for 96 h. The reaction was quenched by liquid nitrogen and THF was added to disperse the black solid. The product was filtered through a 0.2 µm Nylon membrane and washed with THF. The dispersion-filtration-wash process was repeated six times to ensure no un-grafted polymers were left in the residue. Then the dark solids were dispersed in methanol followed by filtration to remove catalyst reagents. The collected product was dried in vacuum at room temperature.

ATRP of iso-BMA in the Presence of GCNF-$CO_2$H

A 25-mL dried round-bottom flask was charged with 0.20 g GCNF-$CO_2$H and 12.3 mg (0.124 mmol) CuCl. The flask was sealed with a rubber septum and degassed and refilled with nitrogen for three times. Deoxygenated acetone (4 mL)

was added into the flask followed by the addition of 26 μL (0.124 mmol) PMDETA via syringe. The mixture was sonicated for 15 min to form a fine dispersion. Then 4 mL (24.7 mmol) deoxygenated iso-butyl methacrylate was added into the flask via syringe, and the mixture was stirred for 5 min. Finally, 30 μL (0.247 mmol) HEBP was added via syringe, and the flask was put into a 50° C. oil bath for 20 h. The reaction was quenched by liquid nitrogen, and THF was added to disperse the black solids. The product was filtered through a 0.2 μm Millipore Nylon membrane and washed with THF. The filtrate was passed through an alumina column, rotary evaporated to remove the solvent, and vacuum dried at 50° C. overnight. The solid residue was purified by repeating dispersion-filtration-wash process THF four times to ensure no un-grafted polymers were left in the residue. The collected solid was dried in vacuum at room temperature overnight.

Synthesis of GCNF-Poly(tert-Butyl Acrylate) (GCNF-PtBA)

Figure 9:
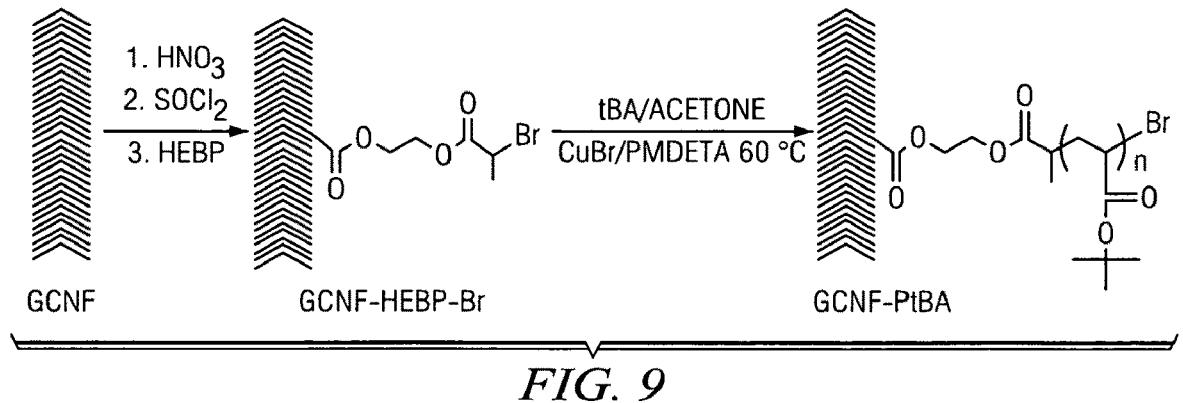
FIG. 9 illustrates a process strategy for synthesis of PtBA brushes on the surface of herringbone GCNFs.

FIG. 9 shows a strategy for synthesis of PtBA brushes on the surface of herringbone GCNFs. A 25-mL dried round-bottom flask was charged with 0.20 g GCNF-HEBP-Br and 38.7 mg (0.27 mmol) CuCl. The flask was sealed with a rubber septum and degassed and refilled with nitrogen for three times. Deoxygenated acetone (4 mL) was added into the flask followed by the addition of 56.6 μL (0.27 mmol) PMDETA via syringe. The mixture was sonicated for 15 min to form an even dispersion. After the addition of 4 mL (27 mmol) deoxygenated tert-butyl acrylate via syringe, the flask was put into a 60° C. oil bath for 22 h. The purification process of the product was the same as that of GCNF-PiBMA.

ATRP of t-BA in the Presence of GCNF-CO$_2$H

A 25-mL dried round-bottom flask was charged with 0.20 g GCNF-COOH and 38.7 mg (0.27 mmol) CuBr. The flask was sealed with a rubber septum and degassed and refilled with nitrogen for three times. Deoxygenated toluene (4 mL) was added into the flask followed by the addition of 56.6 μL (0.27 mmol) PMDETA via syringe. The mixture was sonicated for 15 min to form an even dispersion. Then 4 mL (27 mmol) deoxygenated tert-butyl acrylate was added into the flask via syringe, and the mixture was stirred for 5 min. Finally, 30 μL (0.27 mmol) MBrP was added via syringe, and the flask was put into a 60° C. oil bath for 22 h. The purification process of the product was the same as that of GCNF-PiBMA.

ATRP of t-BA (PtBA)

A 25-mL dried round-bottom flask was charged with 38.7 mg (0.27 mmol) CuBr. The flask was sealed with a rubber septum and degassed and refilled with nitrogen for three times. Deoxygenated acetone (4 mL) was added into the flask followed by the addition of 56.6 μL (0.27 mmol) PMDETA via syringe. Then 4 mL (27 mmol) deoxygenated iso-butyl acrylate was added into the flask via syringe, and the mixture was stirred for 5 min. Finally, 30 μL (0.27 mmol) MBrP was added via syringe, and the flask was put into a 60° C. oil bath for 22 h. The reaction was quenched by liquid nitrogen, and acetone was added to dilute the mixture. Catalyst was absorbed by passing the solution through an alumina column, and the solvent was removed by rotary evaporation. The polymer product was dried in vacuum at 50° C. overnight.

Preparation of GCNF-Poly(Acrylic Acid) (GCNF-PAA)

Hydrophilic poly(acrylic acid) brushes on the surface of GCNFs were obtained by acidic hydrolysis of PtBA chains in the GCNF-PtBA sample into PAA brushes. Typically, 50 mg of GCNF-PtBA was dispersed into 15 mL CHCl$_3$ in a 25-mL flask and 2.5 mL CF$_3$CO$_2$H was added thereafter. The mixture was stirred at room temperature for 24 h under nitrogen protection. The reaction mixture was rotary evaporated under vacuum to remove the reagents, and the black powder of GCNF-PAA was collected and dried in vacuum at room temperature.

Synthesis of GCNF-Poly(Glycidyl Methacrylate) (GCNF-PGMA)

Figure 10:
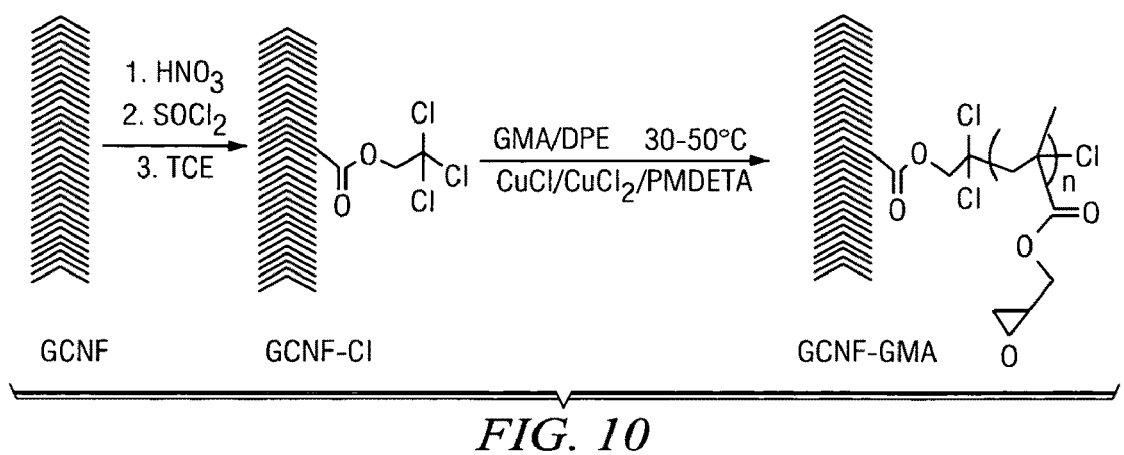
FIG. 10 illustrates a process strategy for synthesis of PGMA brushes on the surface of herringbone GCNFs.

FIG. 10 shows a strategy for synthesis of PGMA brushes on the surface of herringbone GCNFs. A 15-mL round-bottomed flask, with a magnetic stir bar, was charged with 8.0 mg (0.060 mmol) CuCl$_2$ and 0.20 g GCNF-Cl. The flask was sealed with a rubber septum and degassed and refilled with N$_2$ three times. Deoxygenated DPE (4 mL) was added into the flask followed by three freeze-pump-thaw cycles to remove adsorbed oxygen. The mixture was sonicated 10 min to form a uniform dispersion. A 10-mL round-bottomed flask was charged with 60.0 mg (0.604 mmol) CuCl. The flask was sealed with a rubber septum and degassed and refilled with N$_2$ three times. 4 mL (30.2 mmol) deoxygenated GMA and 140 μL (0.664 mmol) PMDETA were added into the flask via syringe and the mixture was stirred for 15 min to form a green homogeneous solution. The monomer solution was transferred into the GCNF-Cl dispersion flask by cannula. The flask was put into room temperature water bath for 24 h. CHCl$_3$ was added to dilute the reaction mixture and unreacted monomers were removed by centrifuge. The solid residue was redispersed in CHCl$_3$/MeOH (9/1, v/v) solvent mixture and centrifuged six times to remove ungrafted polymers and catalyst. The solid product of GCNF-PGMA was collected and dried in vacuum oven overnight at room temperature.

Three types of GCNFs with herringbone, platelet, and ribbon structures, have been prepared by chemical vapor deposition of carboneous gases on metal nanoparticles. In this work, however, herringbone GCNFs are used to demonstrate the preparation of polymer brushes on the surface of GCNFs because: (1) herringbone GCNFs have a high number density of surface reactive sites, (2) herringbone GCNFs are prepared in higher yield than that of GCNFs with the other two structures. The herringbone GCNFs were prepared by catalytic deposition of ethylene at 600° C. using Fe/Cu alloy nanoparticles as catalyst. Surface-oxidation of as-prepared GCNFs is carried out in concentrated nitric acid to introduce reactive carboxyl groups on the GCNF surface. Studies on GCNFs surface oxidation with nitric acid indicate that the structure of individual nanofiber remains intact after surface treatment. However, BET specific surface area of oxidized nanofibers, especially herringbone GCNFs, increases significantly due to enhancement of the nanofiber surface roughness as a result of edge-site etching of graphitic sheets which are stacked along the long nanofiber axis. Oxidized GCNFs have a specific surface area value of ca. 25.56 m$^2$/g compared with ca. 15.31 m$^2$/g for as-prepared GCNFs. Oxidized GCNFs have 6.6 carboxylic groups per 1000 carbon atoms based on the element analysis results shown in Table 3. Therefore, the number of carboxylic groups per unit surface area is ca. $1.3 \times 10^{19}$ groups per square meter (13 groups/nm$^2$), which is consistent with the literature value of 2.5×10$^{19}$ oxygen atoms per square meter.

Carboxyl groups on the surface of oxidized GCNFs are converted to acyl chloride groups with SOCl$_2$ followed by reaction with HBBP or HEBP to immobilize ATRP initiators onto the surface of GCNFs, respectively. Elemental analysis confirms the presence of bromine atoms in GCNF-HBBP-Br nanofibers at ca. 0.92 wt %, which is equal to ca. 3.1×10$^{18}$ bromine atoms per square meter (3.1 Br/nm$^2$), whereas the surface coverage for GCNF-HEBP-Br is ca. 1.7×10$^{18}$ bromine atoms per square meter (1.7 Br/nm$^2$) and for GCNF-Cl is ca. 8.0×10$^{17}$ chlorine atoms per square meter (0.8 Cl/nm$^2$).

TABLE 3

Elemental analysis results of GCNFs and relative materials

| | Element | | | | | |
|---|---|---|---|---|---|---|
| | C (wt %) | H (wt %) | O (wt %) | N (wt %) | Br (wt %) | Cl (wt %) |
| GCNFs | 95.78 | 0.29 | 0.22 | — | — | — |
| GCNF-CO$_2$H | 91.84 | 0.50 | 7.4 | 0.26 | — | — |
| GCNF-HBBP-Br | 90.64 | 0.74 | 6.09 | — | 0.92 | — |
| GCNF-HEBP-Br | 92.89 | 0.45 | 5.98 | 0.18 | 0.50 | — |
| GCNF-Cl | 93.52 | 0.42 | 5.03 | — | — | 1.03 |

GCNF-Poly(n-Butyl Acrylate) Brushes (GCNF-PBA)

ATRP of acrylate and methacrylate monomers have been used to prepare polymer brushes on solid substrates. Liu, et al. reported the first synthesis of polymer brushes on the surface of carbon black particles by in situ ATRP of n-butyl acrylate. Since carbon black particles themselves react as radical-scavenging reagents, the polymerization rate of the ATRP of n-butyl acrylate in the presence of unfunctionalized carbon black particles was 10 times lower than that of normal ATRP of n-butyl acrylate in the absence of carbon black particles. When ATRP of n-butyl acrylate was initiated by immobilized initiators on the surface of carbon black particles, the polymerization rate was even slower. Similar results are obtained in our experiments (see Table 4). ATRP of n-butyl acrylate is performed in bulk at 70° C. with CuBr/PMDETA complex as catalyst. Different monomer/GCNF-HBBP-Br ratios and monomer/catalyst ratios are used to carry out the polymerization. The polymerization rate is so slow that only 35 wt % polymer content is obtained even after 263 h of reaction for GCNF-PBA4.

TABLE 4

Conditions and results of ATRP of n-butyl acrylate initiated by GCNF-HBBP-Br.

| Sample | [nBA]:[I][a] | Catalyst Ratio[b] | Temp (° C.) | Time (h) | PBA wt %[c] |
|---|---|---|---|---|---|
| GCNF-PBA1 | 3400:1 | 200:1:1 | 70 | 168 | 11 |
| GCNF-PBA2 | 3400:1 | 10:1:1 | 70 | 96 | 17 |
| GCNF-PBA3 | 340:1 | 10:1:1 | 70 | 116 | 34 |
| GCNF-PBA4 | 750:1 | 10:1:1 | 70 | 263 | 35 |

[a]Molarity of immobilized initiators calculated by (weight of GCNF-HBBP-Br × 0.115 mmol/g).
[b]Catalyst Ratio = [nBA]:[CuBr]:[PMDETA].
[c]Obtained from TGA curves.

At the late stage of polymerization, viscosity of the reaction mixture increases due to the interaction between polymer chains grafted from the surface of GCNFs. A similar phenomenon was observed when polymer brushes grew from the surface of carbon black particles and carbon nanotubes.

Figure 11:
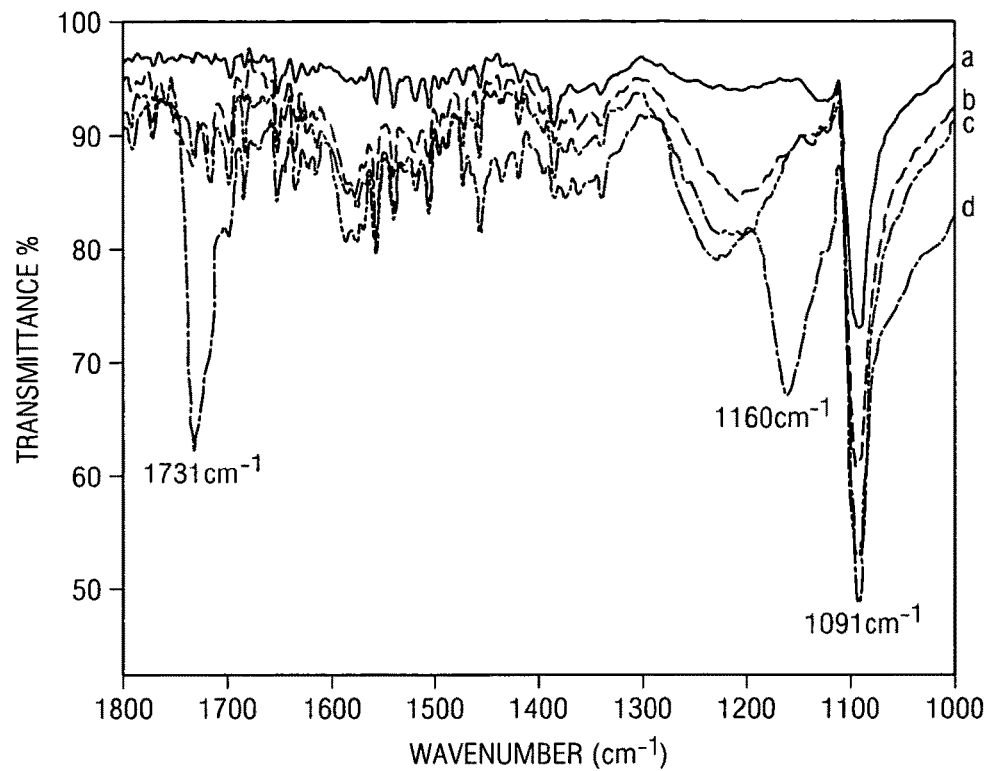
FIG. 11 illustrates FT-IR spectra of (a) GCNFs, (b) GCNF-HBBP-Br, (c) GCNF-$CO_2H$ and (d) GCNF-PBA4.

Surface-functionalization of GCNFs can be detected by FT-IR spectra recorded with KBr plates as shown in FIG. 11. The characteristic bands of as-prepared GCNFs are discussed in detail elsewhere. The intensive 1091 cm$^{-1}$ and broad 1217 cm$^{-1}$ bands are assigned to the C—C stretching vibration, while the weak band at 1580 cm$^{-1}$ is attributed to the vibration of aromatic rings in graphitic sheets. After oxidation, new bands at 1716 cm$^{-1}$ and 1731 cm$^{-1}$ appear in the spectrum of GCNF-CO$_2$H, which are assigned to the C=O stretching in the form of carboxyl and ester groups, respectively. Meanwhile, the intensity of the 1217 cm$^{-1}$ band is greatly enhanced because C—O stretching and O—H bending bands also fall in this region. The GCNF-HBBP-Br spectrum is very similar to that of GCNF-CO$_2$H except that there is a slight enhancement of the 1731 cm$^{-1}$ band, which is consistent with the elemental analysis result that only ca. 24.2% carboxyl groups have been converted to initiator molecules. Since poly(n-butyl acrylate) brushes have been grafted from the surface of GCNFs, characteristic absorption bands of poly(n-butyl acrylate) are expected to appear in the GCNF-PBA4 spectrum. Intensity of the 1731 cm$^{-1}$ band increases significantly due to C=O stretching band and a new absorption band at 1160 cm$^{-1}$ is clearly observed, which is associated with the C—O stretching vibration of n-butyl ester groups.

Figure 12:
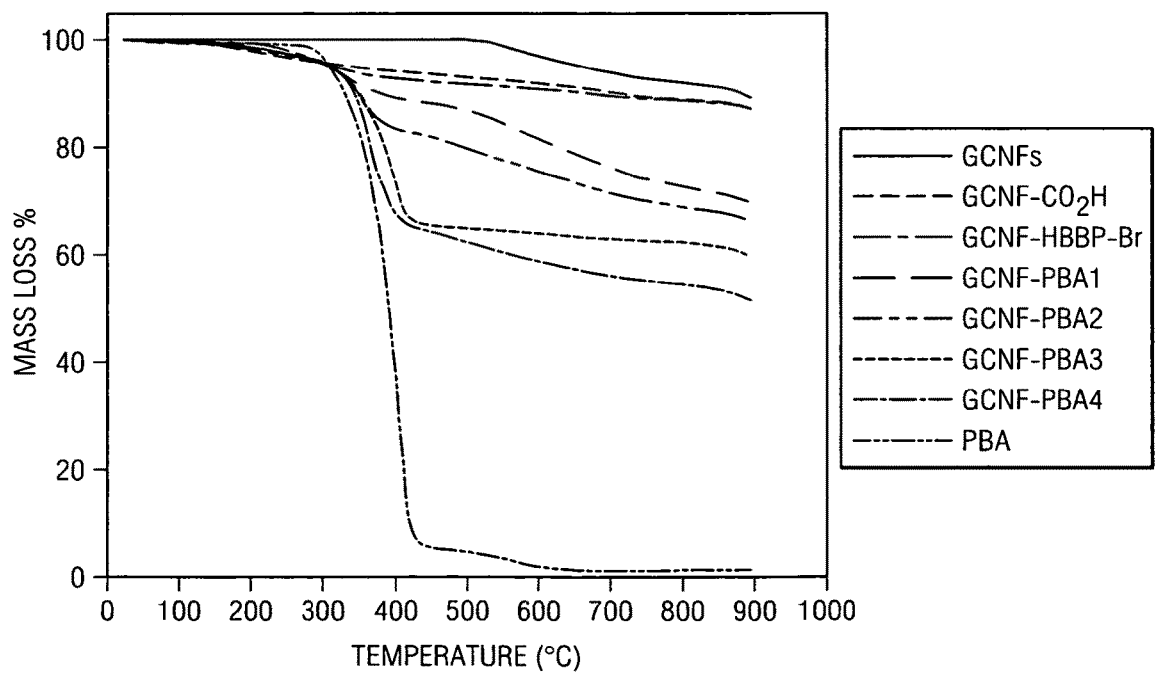
FIG. 12 illustrates TGA curves of as-prepared GCNFs, surface-functionalized GCNFs, and PBA.

FIG. 12 illustrates the sequential TGA curves of as-prepared GCNFs, oxidized GCNFs, initiator-immobilized GCNFs, poly(n-butyl acrylate) brushes-functionalized GCNFs, and pure poly(n-butyl acrylate), respectively. TGA analysis was carried out under a nitrogen gas atmosphere to avoid oxidation of the samples by oxygen present in air.

For as-prepared GCNFs, no mass-loss can be observed before the onset at 570° C. due to the excellent thermal stability of the tightly stacked structure of graphitic sheets in GCNFs, whereas the mass-loss of about ca. 10.6% from 570° C. to 900° C. is attributed to the release of hydrocarbon moieties from hydrogen terminated edge-sites on GCNFs surface. Surface oxidation introduces oxygen atoms onto the surface of GCNFs by etching the edge of graphitic sheets. Surface carboxyl groups are less stable than the aromatic rings of graphite in the thermal gravimetric analysis environment. Therefore, CO$_2$ and CO are gradually released when temperature increases from 150° C. to 900° C. The GCNF-Br curve has a similar profile as that of GCNF-CO$_2$H because the small amount of immobilized initiator molecules in GCNF-HBBP-Br sample can result in only a slightly enhanced mass-loss.

Unlike GCNF-CO$_2$H and GCNF-HBBP-Br samples, the TGA curves of GCNF-PBA samples exhibit sharp mass-loss events from 330° C. to 400° C. Rapid mass-losses in this temperature region are clearly associated with PBA polymer brushes as shown by the characteristic pure PBA mass-loss profile centered at 400° C. Polymer content of each GCNF-PBA sample, GCNF-PBA1-GCNF-PBA4, can thus be determined from this mass-loss event, as shown in Table 4.

When as-prepared GCNFs or oxidized GCNFs are dispersed into an organic solvent such as chloroform, THF, or acetone, they precipitate from the dispersion in less than 10 min. The dispersibility of GCNF-HBBP-Br or GCNF-HEBP-Br nanofibers in organic solvents is slightly enhanced due to the presence of surface-immobilized organic molecules, but these nanofibers also precipitate out after several hours. However, the presence of poly(n-butyl acrylate) brushes on the surface of GCNFs significantly improves the dispersibility of GCNF-PBA samples in common organic solvents such as THF, chloroform, and toluene (see FIG. 13). When GCNF-PBA samples are dispersed into strong polar solvents such as methanol, DMF, and DMSO, which are known to be poor solvents for poly(n-butyl acrylate), nanofibers precipitate immediately.

Figure 14:
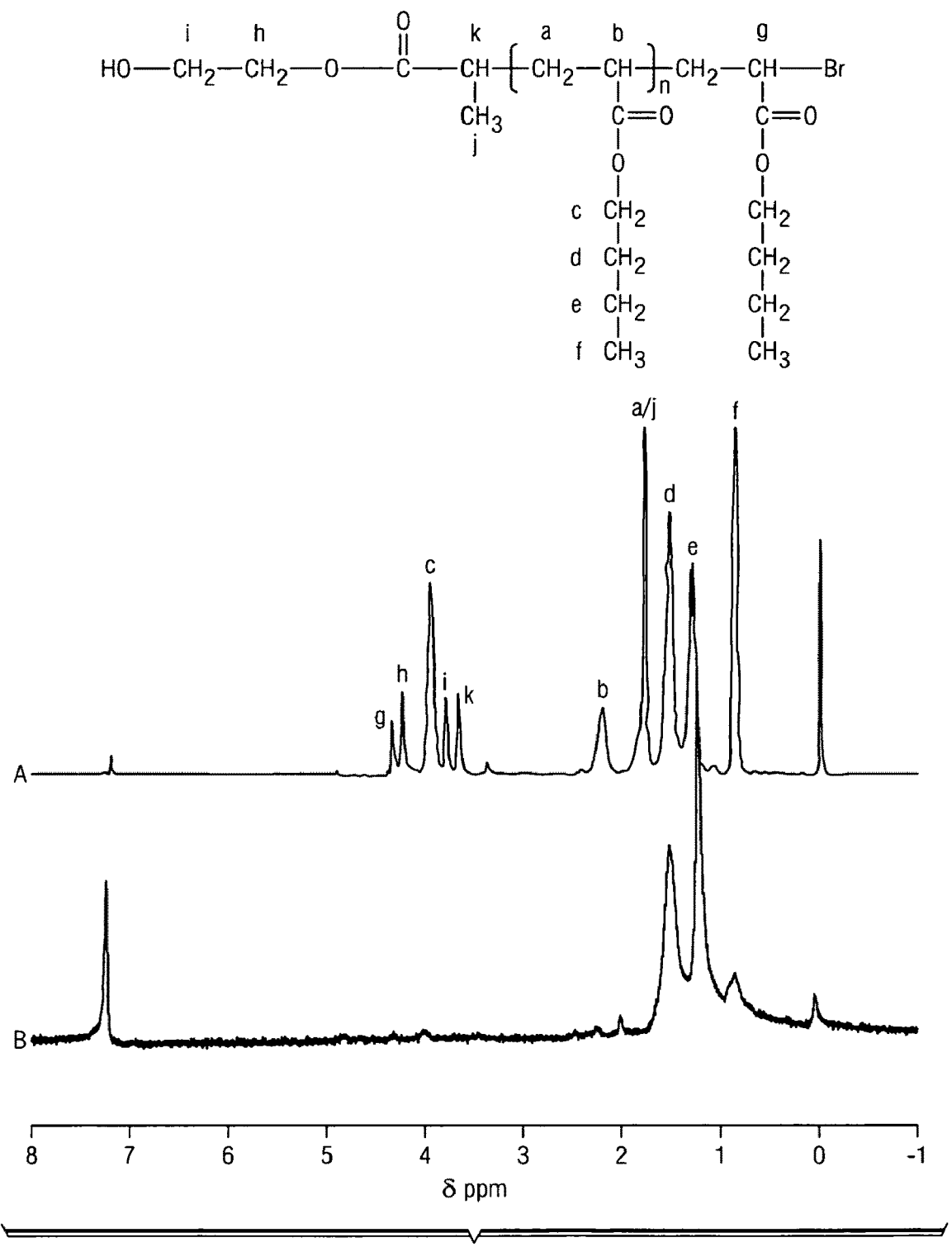
FIG. 14 illustrates H-NMR spectra of (A) PBA, (B) GCNF-PBA3 in $CDCl_3$.

Comparison of the two $^1$H-NMR spectra shown in FIG. 14 indicates the presence of poly(n-butyl acrylate) in GCNF-PBA3. The proton signals at 0.91 ppm, 1.34 ppm, and 1.58 ppm in the spectrum of GCNF-PBA3 are assigned to the methyl and methylene groups of the n-butyl side chain of the poly(n-butyl acrylate), respectively. Compared with the spectrum of pure PBA, intensities of signals corresponding to the backbone protons are dramatically reduced in the GCNF-PBA3 spectrum due to poor relaxation of nuclear spins of surface-bound polymer chains with restricted motions.

Direct evidence for polymer brush formation on the surface of GCNFs comes from transmission electron microscopy (TEM) analysis. FIGS. 15A-C show TEM images of as-prepared GCNFs and GCNF-PBA3. At lower magnification, the diameter of individual nanofibers ranges from ca. 30 nm to ca. 200 nm because of the broad size distribution of the growth catalyst Fe/Cu alloy particles.

Individual nanofibers of GCNF-PBA3, imaged in high contrast, are covered by polymer layers of lower contrast, which are formed by the polymer brushes wrapping around the surface of nanofibers. However, polymer layer thickness varies from nanofiber to nanofiber and even along different regions of a single nanofiber. Variation in polymer layer thickness, a phenomenon not observed with carbon nanotube/polymer brushes, is caused by the rugged morphology of the surface of GCNFs. During the oxidation process, defects at the edge sites of GCNFs surface are more vulnerable for oxidation attack and the local concentrations of carboxyl groups near such defective areas are expected to be higher. Consequently, a higher concentration of immobilized initiator molecules occurs near these local regions during surface derivatization. According to the mechanism of ATRP, higher initiator concentration results in higher polymerization rate. Therefore, longer polymer chains grow at these surface defect sites.

The measured molecular weight and polydispersity of PBA brushes cleaved from the surface of GCNF-PBA4 sample (Mw=31,300, Mw/Mn=1.73) are consistent with the TEM observation of polymer layers on individual GCNFs with variable thickness. Based on the BET surface area of oxidized GCNFs (26 m$^2$/g), an average surface density of the polymer brush chains in GCNF-PBA4 polymer brushes is calculated to be ca. 3 polymer chains/1.0 nm$^2$. As an ideal stacking pattern of graphene sheets contains ca. 120 unsaturated edge carbon atoms/10 nm$^2$, ca. 1 of every 40 GCNF surface edge sites is functionalized with a polymer chain.

Figure 16:
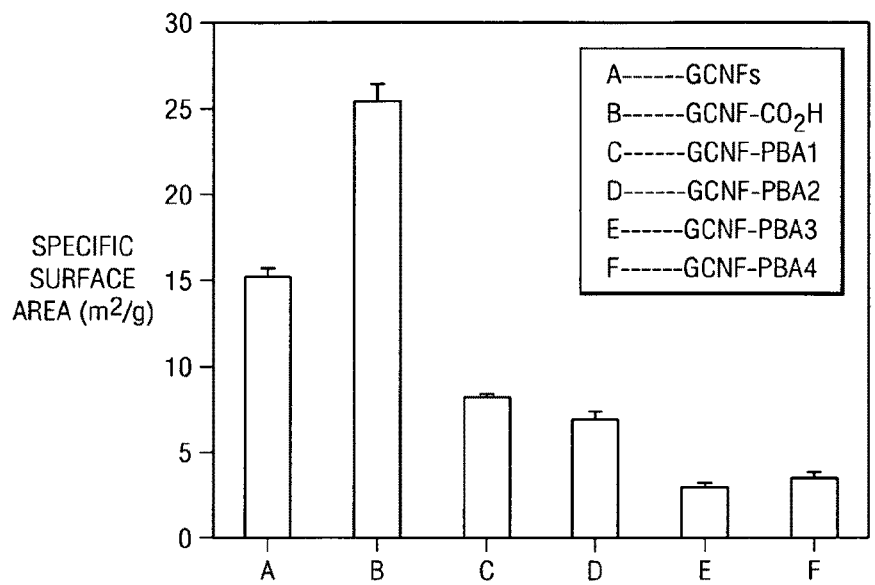
FIG. 16 illustrate BET specific surface area of (A) GCNFs, (B) GCNF-$CO_2H$, (C) GCNF-PBA1, (D) GCNF-PBA2, (E) GCNF-PBA3, (F) GCNF-PBA4.

On the other hand, polymer brushes enwrapped on the nanofiber surface have a remarkable effect on GCNF surface morphology. As shown in FIG. 16, GCNF-PBA samples have a much smaller value of specific surface area than GCNF-CO$_2$H and as-prepared GCNFs, because the rugged surfaces of GCNFs are now covered by a smooth polymer layer. Moreover, the specific surface area decreases as polymer brush content increases due to this surface-smoothing effect.

To prove that these polymer brush chains are covalently grafted from the surface of GCNFs by surface initiated ATRP, two control experiments are carried out. Polymerizations of n-butyl acrylate initiated by free HBBP initiators are performed in the presence of as-prepared GCNFs and oxidized GCNFs, respectively, under identical conditions used for bulk polymer ATRP (sample PBA0). The polymerizations are quenched by liquid nitrogen, and the reaction mixtures are dispersed in THF, filtered, and washed with THF repeatedly. The black solids are collected and labeled as c-GCNFs and c-GCNF-CO$_2$H, respectively. The obtained filtrates are further purified by passing through an alumina column followed by vacuum drying to give the corresponding polymer products, PBA1 and PBA2, respectively.

TABLE 6

Conditions and results of ATRP of nBA initiated by HBBP.

| Sample | [nBA]:[CuBr]:[PMDETA]:[HBBP] | Temp (° C.) | Time (h) | Mw | Mw/Mn | Yield |
|---|---|---|---|---|---|---|
| PBA0 | 50:1:1:1 | 70 | 2 | 19,800 | 1.23 | 99.1% |
| PBA1$^a$ | 50:1:1:1 | 70 | 2 | 13,400 | 1.30 | 58.5% |
| PBA2$^b$ | 50:1:1:1 | 70 | 20 | 24,700 | 1.53 | 98.6% |

$^a$In the presence of as-prepared GCNFs, [BA]:[GCNFs] = 10:1 (wt/wt).
$^b$In the presence of GCNF-CO$_2$H, [BA]:[GCNF-CO$_2$H] = 10:1 (wt/wt).

Figure 17:
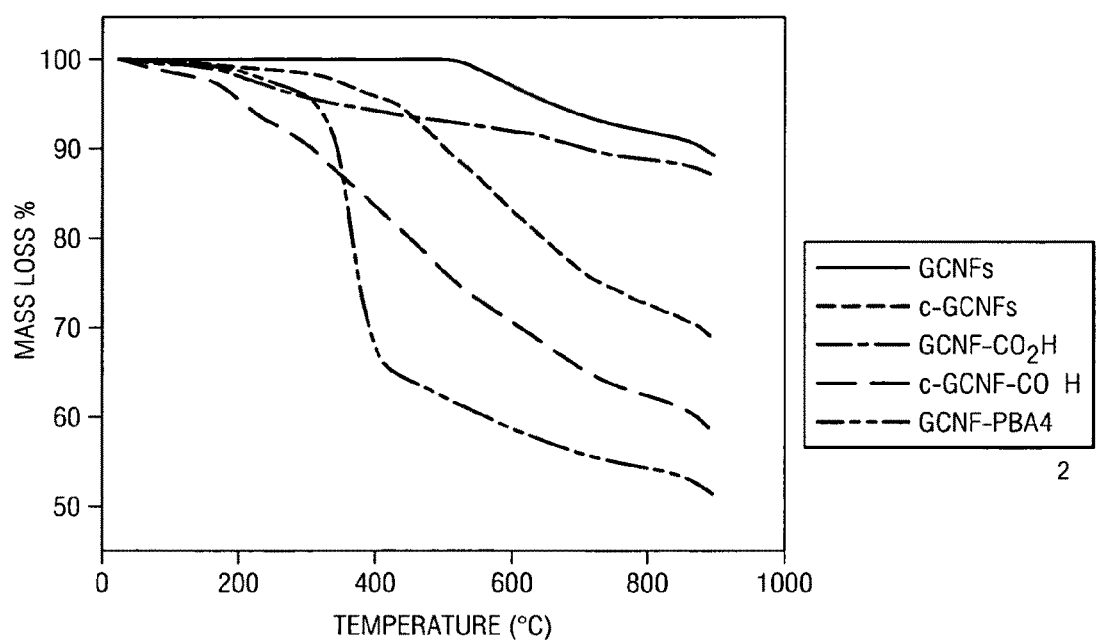
FIG. 17 illustrates TGA curves of GCNFs, c-GCNFs, GCNF-$CO_2H$, c-GCNF-$CO_2H$, and GCNF-PBA4 samples.

Molecular weight and polydispersity of these PBA samples obtained from GPC (see Table 6) indicate that the presence of as-prepared GCNFs or GCNF-CO$_2$H nanofibers had a negative effect on ATRP polymerization of n-BA, giving lower polymerization rates and broader polymer chain molecular weight distributions. Furthermore, TGA curves of the c-GCNFs and c-GCNF-CO$_2$H samples are quite different from those of as-prepared GCNFs and GCNF-CO$_2$H nanofibers. The c-GCNF curve has a ca. 31% mass-loss compared with the ca. 10.6% mass-loss observed for as-prepared GCNFs, and similar comparison is notable for c-GCNFs and as-prepared GCNFs in FIG. 17. These results indicate that some oligomer fragments are covalently attached on the nanofiber surface during the polymerization process. Because GCNFs are radical scavengers, it is unavoidable that some oligomer radicals formed at the beginning stage of ATRP process are trapped by GCNFs. However, the sharp mass-loss profile from 330° C. to 400° C. for polymer chains of PBA, is not observed in neither c-GCNF nor c-GCNF-CO$_2$H nanofibers, indicating that without surface immobilized initiators, GCNF and GCNF-CO$_2$H nanofibers cannot grow polymer brushes from the surface under the same ATRP conditions.

Figure 18:
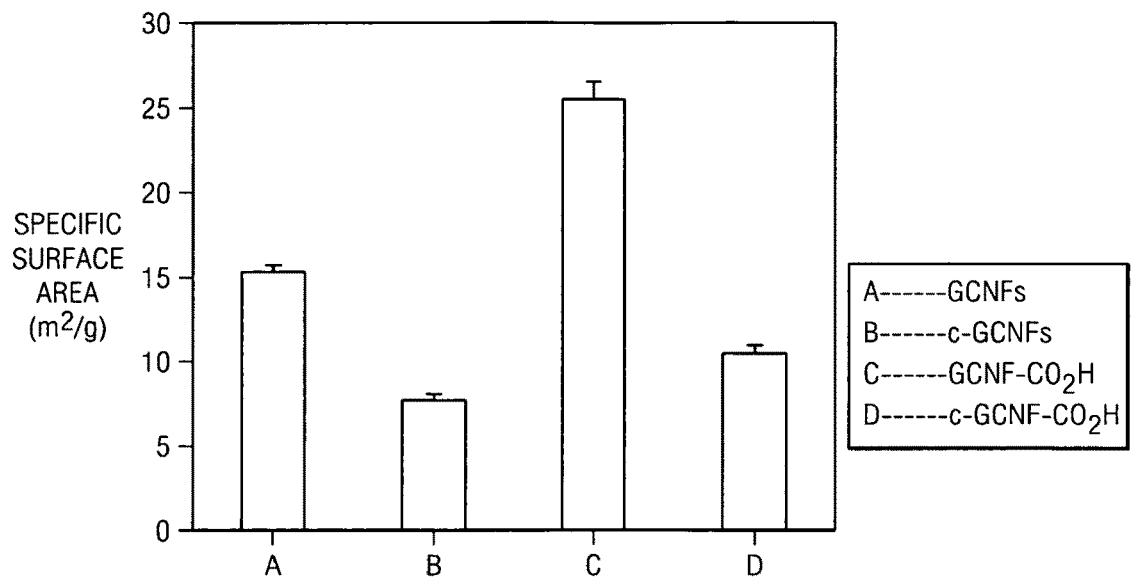
FIG. 18 illustrates BET specific surface area of GCNFs, c-GCNFs, GCNF-$CO_2H$, and c-GCNF-$CO_2H$.

The surface entrapment of oligomer fragments is also supported by the BET specific surface area analysis (see FIG. 18). The c-GCNFs sample has a specific surface area ca. 7.75 m$^2$/g, which is only about half of the GCNFs sample ca. 15.31 m$^2$/g. Likewise, the c-GCNF-CO$_2$H sample has much less specific surface area ca. 10.55 m$^2$/g than that of GCNF-CO$_2$H ca. 25.56 m$^2$/g. This surface smoothing effect is due to the trapped oligomer fragments covering part of the nanofibers surface.

GCNF-Poly (iso-Butyl Methacrylate) Brushes (GCNF-PiBMA)

ATRP of iBMA initiated by GCNF-HEBP-Br is carried out to prepare poly (iso-butyl methacrylate) brushes on the surface of GCNFs. Unlike the in situ ATRP of n-BA in bulk, acetone is used as solvent in ATRP of iBMA to improve solubility of the catalyst complex in relatively nonpolar iBMA. The "halogen exchange" technique is required in ATRP of methacrylate monomers to achieve controlled polymerization, because, while the dormant species are very reactive, the tertiary radicals are relatively stable, resulting in larger equilibrium constant ($K_{eq} = k_{deact}/k_{act}$) and higher concentration of reactive radical species. Matyjaszewski et. al. revealed that an R—Br/CuCl system, which results in fast initiation and deactivation, is generally the best initiator/catalyst pair for ATRP of methacrylate monomers. In this work, since the initiator, GCNF-HEBP-Br, is R—Br based, CuCl is used as the catalyst. The polymerization is effected at 50° C. for 96 h, resulting in a polymer content of 45 wt % in the GCNF-PiBMA sample. A control experiment is also carried out under similar conditions in which ATRP of iBMA is initiated by EBriB in the presence of GCNF-$CO_2$H to give a polymer sample labeled as c-PiBMA-Br (see Table 7). No significant difference is observed between the absence and presence of GCNF-$CO_2$H nanofibers, and controlled molecular weight and narrow polydispersity are obtained for both PiBMA-Br and c-PiBMA-Br.

TABLE 7

Conditions and results of ATRP of iBMA in 50% acetone.

| Sample | [iBMA]:[I] | Catalyst Ratio[d] | T (° C.) | Time (h) | Mn | Mw/Mn | Yield |
|---|---|---|---|---|---|---|---|
| PiBMA-Br | 100:1[b] | 200:1:1:1 | 50 | 20 | 20,200 | 1.17 | 80.1% |
| c-PiBMA-Br[a] | 100:1[b] | 200:1:1:1 | 50 | 20 | 18,700 | 1.19 | 77.8% |
| GCNF-PiBMA | 2000:1[c] | 200:1:1:1 | 50 | 96 | — | — | — |

[a]In the presence of GCNF-$CO_2$H;
[b][I] = [EBriB];
[c][I] = [GCNF-HEBP-Br];
[d]Catalyst Ratio = [iBMA]:[CuCl]:[PMDETA].

Figure 19:
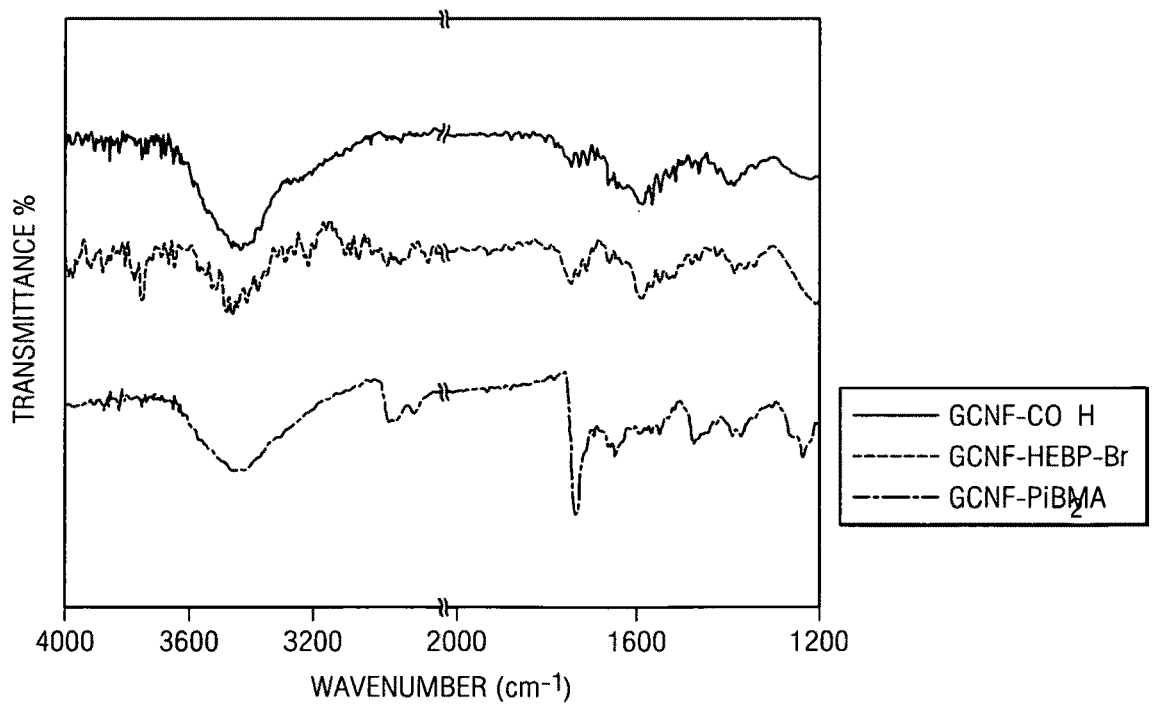
FIG. 19 illustrates FT-IR spectra of GCNF-$CO_2H$, GCNF-HEBP-Br, and GCNF-PiBMA.

Functional moieties on the surface of GCNFs can be identified by FT-IR as shown in FIG. 19. The weak band appearing near 1716 cm$^{-1}$ in the spectrum of GCNF-$CO_2$H is assigned to the C=O stretching from carboxyl groups. The GCNF-HEBP-Br spectrum is very similar to that of GCNF-$CO_2$H except for the presence of the characteristic carboxyl C=O stretching band at 1728 cm$^{-1}$ in the latter spectrum. For the GCNF-PiBMA sample, on the other hand, intensity of 1728 cm$^{-1}$ band increases significantly, and the C—H stretching at 2954 cm$^{-1}$ also increases in intensity, indicating the presence of polymer moieties.

Figure 20:
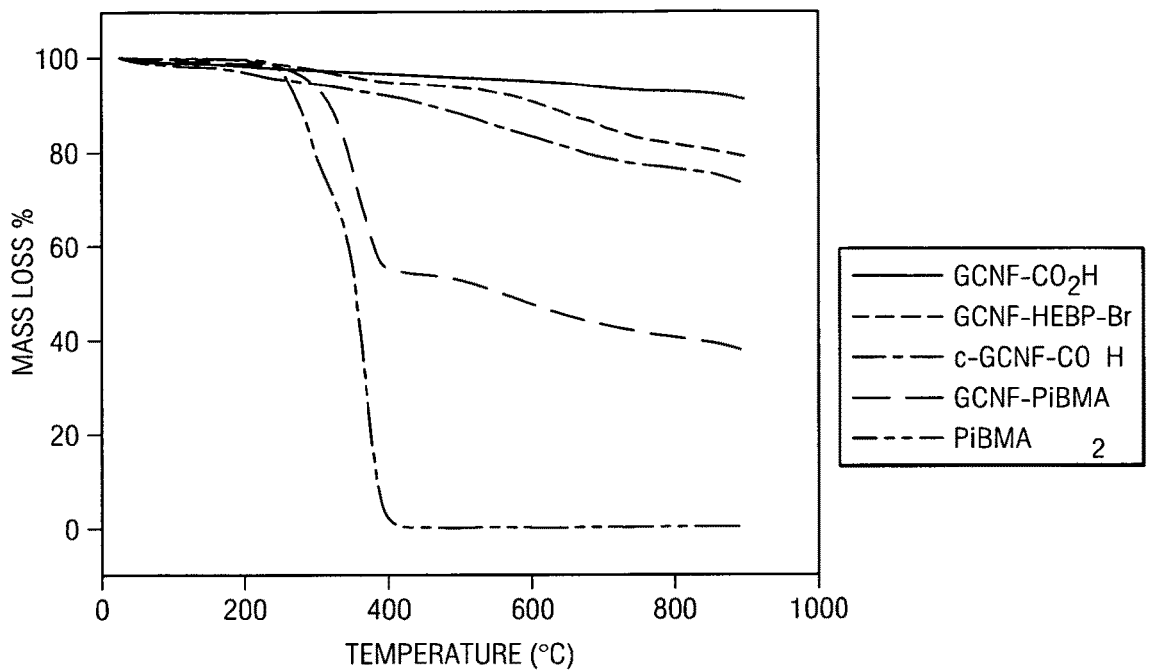
FIG. 20 illustrates TGA curves of GCNF-$CO_2H$, GCNF-HEBP-Br, c-GCNF-$CO_2H$, GCNF-PiBMA, and PiBMA samples.

FIG. 20 shows the TGA curves of GCNF-$CO_2$H, GCNF-HEBP-Br, c-GCNF-$CO_2$H, GCNF-PiBMA, and PiBMA samples recorded under nitrogen. The sharp mass-loss event from 300° C. to 400° C. in the GCNF-PiBMA profile is clearly associated with the decomposition of grafted PiBMA brush, since free PiBMA sample has a characteristic mass-loss in the same temperature range. The profile of the c-GCNF-$CO_2$H sample is different from that of the GCNF-$CO_2$H sample and has a larger mass-loss than GCNF-HEBP-Br in the entire temperature range from 150° C. to 900° C., indicating that oligomer radicals are grafted on the surface of c-GCNF-$CO_2$H during the polymerization process because GCNF-$CO_2$H nanofibers can act as radical scavengers.

Figure 21:
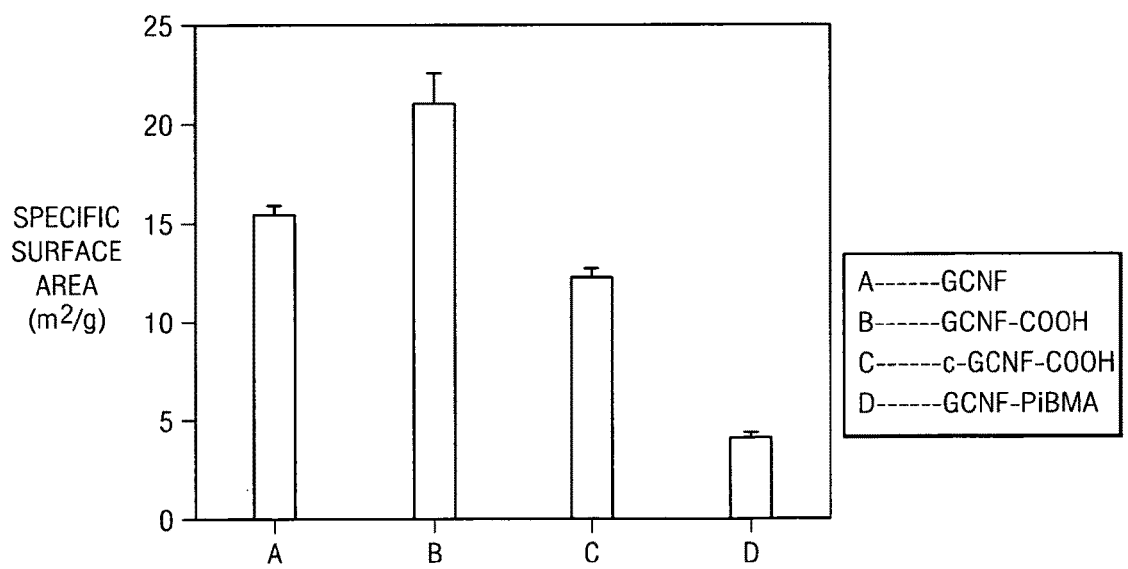
FIG. 21 illustrates BET specific surface area of (A) GCNF, (B) GCNF-$CO_2H$, (C) c-GCNF-$CO_2H$, and (D) GCNF-PiBMA

The c-GCNF-$CO_2$H sample has a specific surface area ca. 12.1 m$^2$/g, much smaller than ca. 20.9 m$^2$/g for GCNF-$CO_2$H (see FIG. 21). FIG. 21 also shows that the specific surface area of GCNF-PiBMA sample is reduced greatly to ca. 4.1 m$^2$/g due to the surface-grafted polymer brushes. The grafted polymer brushes collapse and form a polymer layer around the surface of carbon nanofibers, therefore, the rough surface of GCNF-$CO_2$H is converted to a smooth polymer coating, resulting in much smaller specific surface area for the GCNF-PiBMA sample.

FIGS. 22A-B present the TEM images of individual nanofiber of GCNF-PiBMA. It is clear that the GCNF-PiBMA nanofiber (dark contrast) is covered by a polymer layer (lighter contrast). The polymer layer is formed by polymer brushes wrapping around the nanofiber surface and, as found in GCNF-PBA nanofibers, thickness of this polymer layer varies along the nanofiber. For example, the thickness of polymer layer increases from around 30 nm to about 50 nm along the nanofiber.

Dispersibility test of GCNF-PiBMA samples in a series of organic solvents with various polarities confirms dramatic improvement of carbon nanofiber dispersibility in nonpolar and weak polar solvents. As shown in FIG. 23, GCNF-$CO_2$H nanofibers precipitate from carbon tetrachloride immediately after a sonication treatment, whereas GCNF-PiBMA samples form stable dispersions in carbon tetrachloride, toluene, and acetone. GCNF-PiBMA does not disperse in polar solvent of methanol, as methanol does not dissolve PiBMA polymer chains very well.

GCNF-Poly (tert-Butyl Acrylate) Brushes (GCNF-tBA) and GCNR-Poly (Acrylic Acid) Brushes (GCNF-PAA)

As described above, the in situ ATRP strategy is successful in synthesis of both polyacrylate and polymethacrylate brushes on the surface of GCNFs. For applications in biological fields, hydrophilic polymer brushes are desirable for enhancement of the dispersability of GCNFs in aqueous media. To synthesize hydrophilic polymer brushes on the surface of GCNFs, hydrophobic PtBA brushes are firstly synthesized by the in situ ATRP strategy, and then the tert-butyl groups in PtBA chains are removed by hydrolysis with $CF_3CO_2$H to obtain hydrophilic PAA brushes.

TABLE 8

Conditions and results of ATRP of tBA in 50% acetone.

| Sample | [tBA]:[I] | Catalyst Ratio[d] | T (° C.) | Time (h) | Mn | Mw/Mn | Yield | PtBA |
|---|---|---|---|---|---|---|---|---|
| PtBA-Br | 100:1[b] | 100:1:1:1 | 60 | 22 | 7900 | 1.06 | 79.1% | — |
| c-PtBA-Br[a] | 100:1[b] | 100:1:1:1 | 60 | 22 | 3900 | 1.08 | 44.0% | — |
| GCNF-PtBA1 | 2200:1[c] | 100:1:1:1 | 60 | 22 | — | — | — | 18% |
| GCNF-PtBA2 | 2200:1[c] | 100:1:1:1 | 60 | 144 | — | — | — | 23% |

[a]In the presence of GCNF-CO$_2$H;
[b][I] = [MBrP];
[c][I] = [GCNF-HEBP-Br];
[d]Catalyst Ratio = [tBA]:[CuBr]:[PMDETA].

ATRP of t-BA with GCNF-HEBP-Br as initiator is carried out in acetone solution to prepare PtBA brushes on the surface of GCNFs. Polar solvent acetone is used to improve the solubility of catalyst during ATRP polymerization of t-BA.[93] Two samples of GCNF-PtBA are prepared by ATRP of tBA at 60° C. for 22 h and 144 h, respectively (see Table 8). However, no significant viscosity increase of the reaction mixture is observed during the polymerization process for either sample. Polymer brush content in GCNF-PtBA1 and GCNF-PtBA2 is 18 wt % and 23 wt %, respectively.

Figure 24:
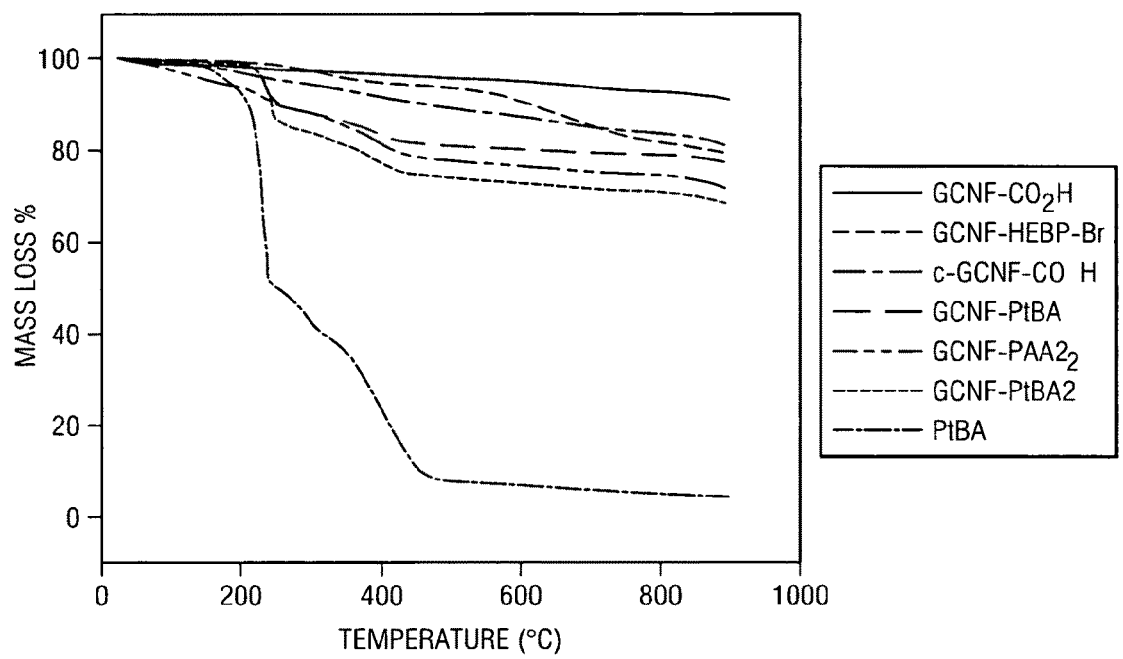
FIG. 24 illustrates TGA curves of GCNF-$CO_2H$, GCNF-HEBP-Br, c-GCNF-$CO_2H$, GCNF-PtBA, GCNF-PAA2, GCNF-PtBA2, and PtBA.

TGA curves of GCNF-PtBA samples shown in FIG. 24 reveal different features from those of GCNF-PBA and GCNF-PiBMA nanofibers. Two sharp mass-loss events are originated from the loss of PtBA brushes: the first one from 200° C. to 240° C. is attributed to dissociation of tert-butyloxygen groups from the PtBA sides chains, while the second mass-loss event from 240° C. to 440° C. is assigned to the gradual decomposition of PtBA backbone atoms. Free polymers of PtBA start to lose mass at only 150° C., which is about 50° C. lower than the PtBA grafted on the surface of GCNFs. Dissociation temperature increase for the PtBA moieties in GCNF-PtBA is attributed to the confined movement of the surface-immobilized polymer chains. TGA curve of GCNF-PAA2 presents a different profile from that of GCNF-PtBA2. Continuous mass-loss of PAA moieties from 100° C. to 440° C. is attributed to the intrinsic low thermal stability of the PAA chains. The smaller polymer content in GCNF-PAA2 is consistent with the loss of tert-butyloxygen groups by hydrolysis of PtBA polymer chains.

Figure 25:
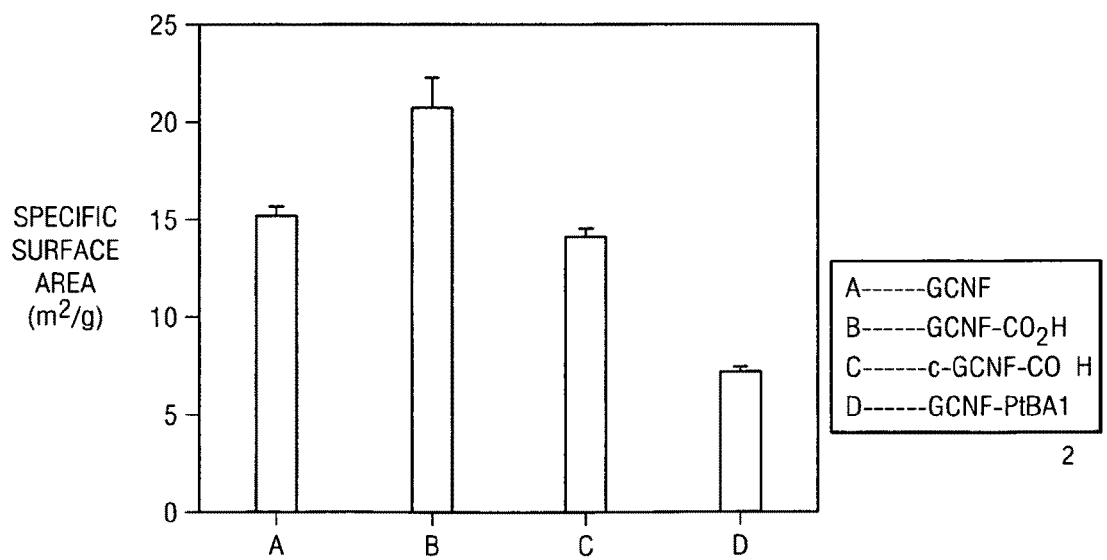
FIG. 25 illustrates BET specific surface area of (A) GCNF, (B) GCNF-$CO_2H$, (C) c-GCNF-$CO_2H$, and (D) GCNF-PtBA samples.

As shown in FIG. 25, the specific surface area of GCNF-PtBA1 is ca. 7.19 m$^2$/g, smaller than that of GCNF-CO$_2$H ca. 20.90 m$^2$/g, because the rugged nanofibers surface is covered by a smooth layer of PtBA brushes. Note that c-GCNF-CO$_2$H also has a smaller specific surface area ca. 14.72 m$^2$/g than that of GCNF-CO$_2$H. As discussed in previous section of GCNF-PBA, oligomer fragments are entrapped on the nanofibers surface during the polymerization process due to the radical scavenger nature of carbon nanofibers and c-GCNF-CO$_2$H nanofibers surface is partially covered by the oligomer fragments, resulting in reduction of specific surface area of nanofibers.

Figure 26:
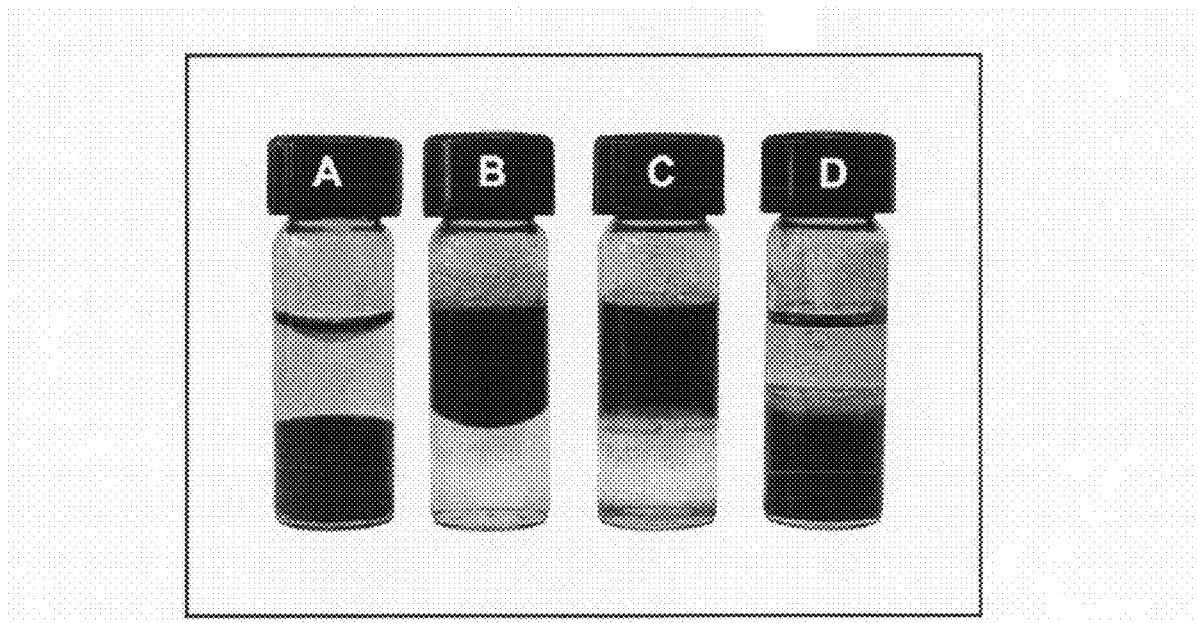
FIG. 26 illustrates a dispersibility test of (A) and (B) GCNF-PtBA2 samples in $H_2O$ (upper)/$CHCl_3$ (lower) and toluene (upper)/$H_2O$ (lower); (C) and (D) GCNF-PAA2 samples in $H_2O$ (upper)/$CHCl_3$ (lower) and toluene (upper)/$H_2O$ (lower).

Dispersibility of GCNF-PtBA samples is greatly improved by surface-grafted PtBA brushes. FIG. 26 reveals that GCNF-PtBA2 forms stable dispersions in CHCl$_3$ and toluene, respectively. When the hydrophobic polymers of PtBA are converted to hydrophilic polymers of PAA, however, the GCNF-PAA2 sample does not dispersed into either CHCl$_3$ or toluene but forms stable dispersion in water.

GCNF-Poly(Glycidyl Methacrylate) Brushes (GCNF-PGMA)

Due to the reactivity of oxirane functional groups, glycidyl methacrylate has been a widely applied commercial monomer and has played a very important role in polymer coatings, adhesives and matrix resins. Homo and copolymers of GMA with controlled molecular weight and low polydispersity have been prepared using ATRP technology and polymerization conditions, such as solvents, catalysts, ligands, and temperatures, have been established. Surface-initiated ATRP of GMA to prepare poly (glycidyl methacrylate) brushes on the surface of silicon wafers has also been reported. Further ring opening of the oxirane side chains of PGMA brushes by primary amine groups has been performed to introduce other functional groups, such as glucose oxidase and alkyl substituents.

To incorporate oxirane groups into GCNF/polymer brushes for applications requiring covalent binding to epoxy resins, surface-initiated ATRP of GMA is carried out to prepare GCNF-PGMA brushes using GCNF-Cl as initiator, CuCl and CuCl$_2$ as catalyst, and PMDETA as ligand. The formed GCNF-PGMA brushes are purified by the same procedures as other GCNF-polymer brushes discussed earlier in this chapter to make sure that no free polymers are absorbed onto the GCNF nanofibers.

Figure 27:
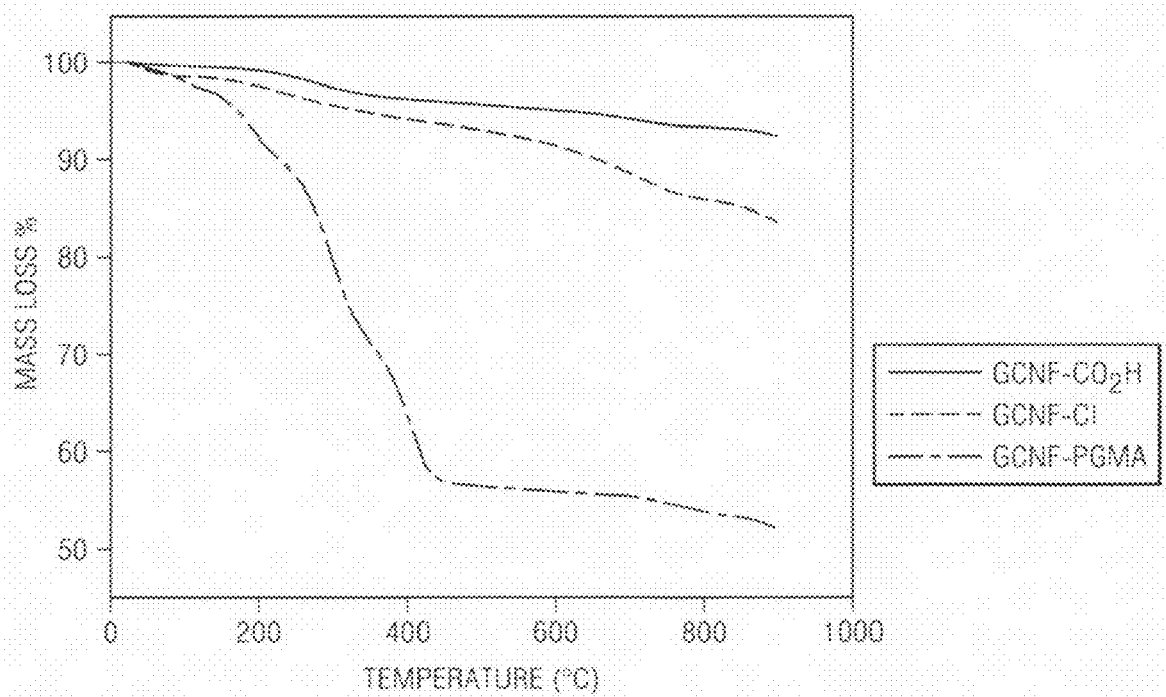
FIG. 27 illustrates TGA curves of oxidized GCNF (GCNF-$CO_2H$), chlorine initiator immobilized GCNF (GCNF-Cl) and PGMA brushes grafted GCNF (GCNF-PGMA).
Figure 28:
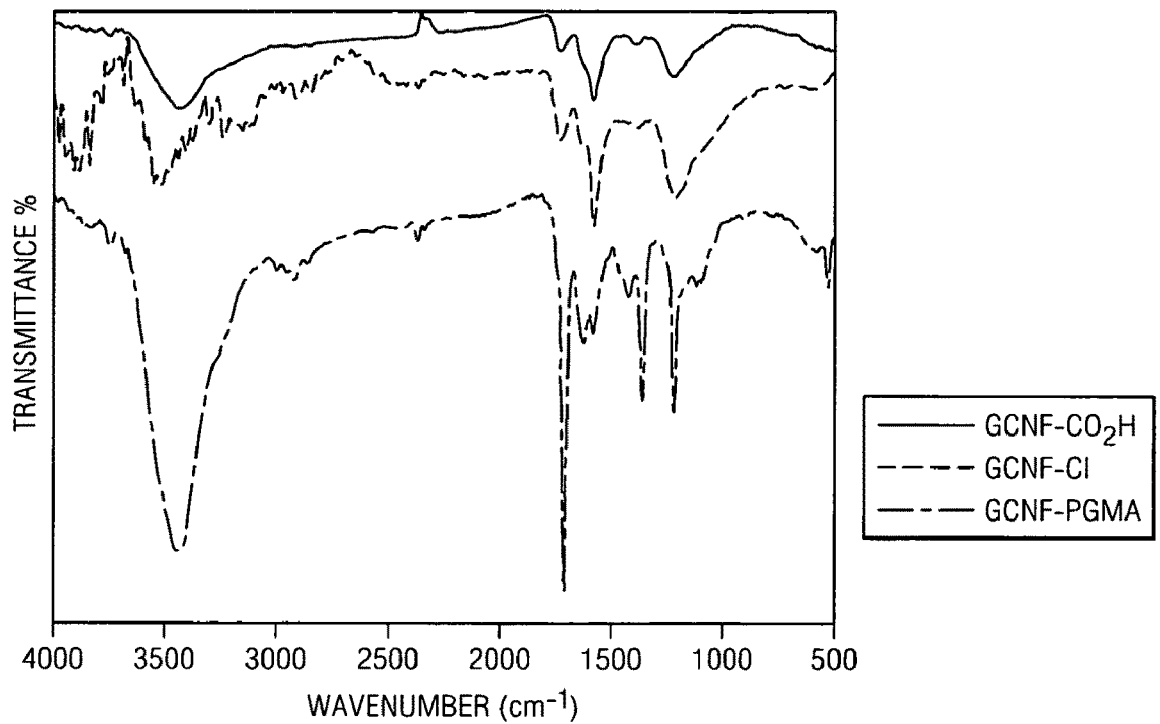
FIG. 28 illustrates FTIR spectra of oxidized GCNF (GCNF-$CO_2H$), chlorine initiator immobilized GCNF (GCNF-Cl) and PGMA brushes grafted GCNF (GCNF-PGMA).

Comparison of TGA curves, shown in FIG. 27, reveals the presence of grafted PGMA brushes in the GCNF-PGMA sample. The mass-loss event from 100° C. to 430° C. is attributed to the thermal decomposition of PGMA chains grafted on the surface of GCNFs. Surface-grafted PGMA brushes are also identified in the FT-IR spectrum of GCNF-PGMA (see FIG. 28). GCNF-Cl nanofibers have a similar spectrum as oxidized GCNF nanofibers, while the spectrum of GCNF-PGMA shows absorption bands at 2933 cm$^{-1}$ and 2865 cm$^{-1}$, characteristic for C—H stretching, and carbonyl C=O stretching band at 1716 cm$^{-1}$ with high intensity from ester groups in the PGMA polymer chains.

Polymerization conditions for the synthesis of GCNF-PGMA polymer brushes are based on the reported procedures with some minor modifications to optimize ATRP of GMA from the surface of GCNFs. Typical conditions are listed in Table 9. The resultant PGMA brushes have reasonable polymer contents up to ca. 38.1 wt % for GCNF-PGMA3.

TABLE 9

Conditions and results of ATRP of glycidyl methacrylate initiated by GCNF-Cl

| Sample | [GMA]:[I][a] | Catalyst Ratio[b] | Concentration | Temp (° C.) | Time (h) | PGMA wt %[c] |
|---|---|---|---|---|---|---|
| GCNF-PGMA1 | 4575:1 | 100:1:0.1:1.1 | 50% | 30 | 48 | 24.9 |
| GCNF-PGMA2 | 4575:1 | 50:1:0.1:1.1 | 100% | 30 | 24 | 32.1 |
| GCNF-PGMA3 | 4575:1 | 50:1:0.1:1.1 | 50% | 30 | 48 | 38.1 |
| GCNF-PGMA4 | 4575:1 | 50:1:0.1:1.1 | 50% | 50 | 24 | 28.0 |

[a]Molarity of immobilized initiators calculated by (weight of GCNF-Cl $\times$ 3.3 $\times$ 10$^{-5}$ mol/g).
[b]Catalyst Ratio = [GMA]:[CuCl]:[CuCl2]:[PMDETA].
[c]Obtained from the TGA curves.

Figure 29:
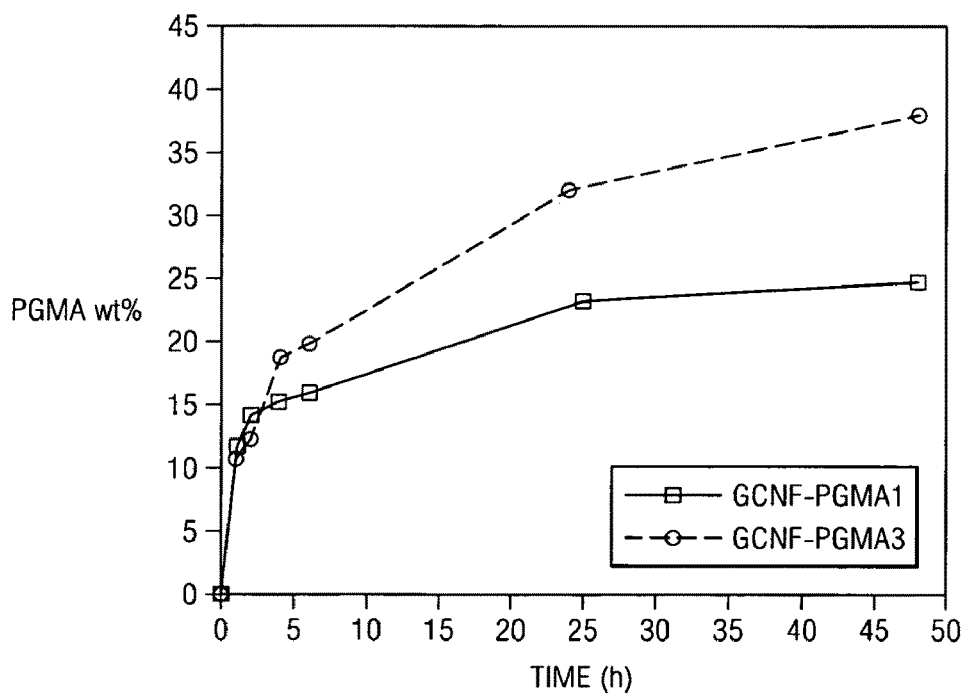
FIG. 29 illustrates dependence of grafted PGMA brushes on the surface of GCNF nanofibers on the polymerization time of surface-initiated ATRP.

Polymerization rate of surface-initiated ATRP of GMA by GCNF-Cl is determined by thermo-gravimetric analysis of samples taken at desired time during the polymerization process. As shown in FIG. 29, the growth rate of polymer brush levels off after about 5 h of polymerization, which means that the polymerization of GMA for either GCNF-PGMA1 or GCNF-PGMA3 is not a true living/controlled ATRP because a plot of polymer content over time should be linear for an ideal ATRP system. The low concentration of initiators on the surface of GCNF fibers might be responsible for the uncontrolled nature of GMA polymerization and the variant local environment on rugged surface of GCNFs also plays an important role in the deviation from normal solution ATRP kinetics. For ATRP, the polymerization rate is proportional to the concentration of both initiator and monomer, so the rate of polymerization for GCNF-PGMA3 is expected to be higher than that of GCNF-PGMA1 because the latter has lower initiator concentration. The same comparison applies to GCNF-PGMA2 and GCNF-PGMA4 because of higher monomer concentration in the former system as shown in Table 9.

Figure 30:
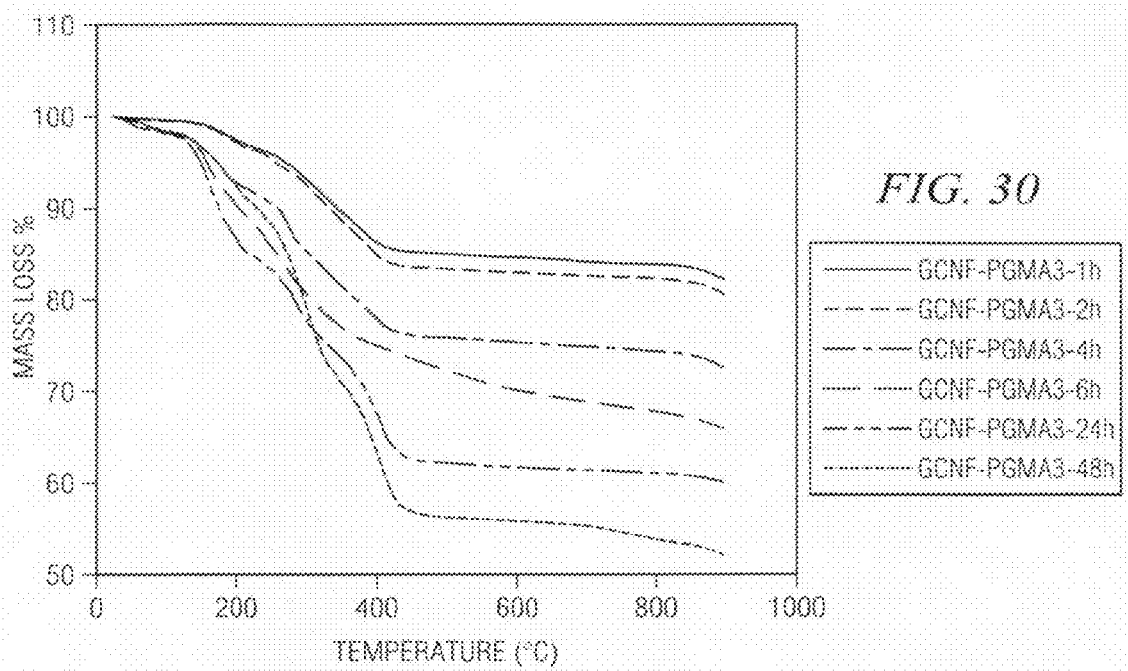
FIG. 30 illustrates TGA curves of GCNF-PGMA3 samples at different time intervals during the 48 h ATRP course.

A series of TGA curves of GCNF-PGMA3 samples taken at different time intervals are shown in FIG. 30. It is notable that these curves have similar profiles with a continuous mass-loss event from 100° C. to 430° C., characteristic for decomposition of PGMA chains, and the mass-loss corresponding to polymer brushes of PGMA increases from about ca. 10 wt % at 1 h to ca. 38.1 wt % at 48 h as the polymerization time increases.

A new strategy for surface-functionalization of GCNFs has been developed by growing polymer brushes from the surface of herringbone GCNFs via in situ ATRP. Sequential surface-functionalization of as-prepared GCNFs by oxidation with nitric acid, acylation with thionyl chloride, and esterification with HBBP, HEBP, or TCE immobilizes ATRP initiator molecules onto the surface of GCNFs. ATRP of n-butyl acrylate initiated by the initiator-immobilized GCNFs affords GCNF-poly (n-butyl acrylate) polymer brushes. ATRP of iso-butyl methacrylate, tert-butyl acrylate, and glycidyl methacrylate in acetone or DPE solution gives the corresponding GCNF-poly(iso-butyl methacrylate), GCNF-poly (tert-butyl acrylate), and GCNF-poly(glycidyl methacrylate) polymer brushes, respectively. Chain length of polymer brushes can be controlled by changing the conditions of in situ ATRP. GCNF-PBA, GCNF-PiBMA, GCNF-PtBA, and GCNF-PGMA polymer brushes form stable dispersions in non-polar and weak-polar organic solvents, such as chloroform, toluene, and acetone, due to the excellent solubility of surface-grafted polymers in these solvents. Acid hydrolysis of GCNF-poly(tert-butyl acrylate) polymer brush forms a hydrophilic GCNF-poly(acrylic acid) polymer brush which has good dispersibility in water.

Graphitic Carbon Nanofiber-Poly(acrylate)
Polymer Brushes as Gas Sensors

The invention can include carbon nanofiber/interdigitated array circuits fabricated with as-prepared herringbone graphitic carbon nanofibers [GCNF], GCNFs surface-derivatized with 3,4'-oxydianiline functional groups [GCNF-ODA], and GCNF-poly(butyl acrylate) [GCNF-PBA] or GCNF-poly(acrylic acid) [GCNF-PAA] polymer brushes are evaluated as solid-state gas sensing materials unsupported by a polymer matrix. Vapor detection is observed as an increase in circuit electrical resistance. Analyte maximum response values exhibit chemoselectivity among different types of GCNF sensors and range over five orders of magnitude in parallel with expected trends in vapor/GCNF van der Waals interaction.

There is a vast literature associated with the use of carbon nanotubes (CNTs) or carbon nanofibers (CNFs) as electrochemical sensors, and several reviews are available. Recent use of carbon nanofiber materials as gas sensors include; gas adsorption by bare CNF arrays, methane detection by CNFs grown on Si(001) surfaces, $NH_3$ and HCl sensing by CNF/polypyrrole coaxial composites, organic vapor detection by CNF/carbon black/polystyrene thin-film composites, and methanol sensing by polyester-grafted CNF/poly(ethylene glycol) thin-film composites. Vapor detection is commonly evidenced by increased electrical resistance within a detector circuit upon exposure to analyte gas. Maximum resistance response values frequently range over five orders of magnitude depending on analyte identity and vapor concentration.

As described in detail above, herringbone graphitic carbon nanofiber (GCNF)-poly(acrylate/methacrylate) polymer brushes can be prepared by atom transfer radical polymerization (ATRP) using a "grafted-from" synthesis strategy. Polymerization of acrylate esters from radical initiators covalently bound to GCNF surface sites affords GCNF-poly(n-butyl acrylate), GCNF-poly(iso-butyl methacrylate) and GCNF-poly(tert-butyl acrylate) polymer brush materials. Acid hydrolysis of the latter forms a GCNF-poly(acrylic acid) polymer brush. GCNF-polymer brush liquid dispersibilities reflect the solubility properties of the pure polymer brush component. GCNF-poly(acrylate or methacrylate esters) disperse in non-aqueous media and are hydrophobic, while the GCNF-poly(acrylic acid) polymer brush is hydrophilic and disperses in water.

The invention can include gas-sensing properties of two GCNF-polymer brushes, GCNF-poly(n-butyl acrylate), GCNF-PBA, and GCNF-poly(acrylic acid), GCNF-PAA, along with that of GCNF materials lacking a polymer brush component for comparison. Milligram quantities of GCNF powders dispersed onto a Pt-wire, interdigitated array (IDA) electrode complete a sensor circuit having a measurable electrical resistance, $R_0$. Exposing these fabricated GCNF/IDA sensors to various analyte vapors increases the measured circuit resistance, $R_v$. Maximum GCNF/IDA detector response, $(R_v-R_0)/R_0$, recorded for a variety of analyte vapors range over five orders of magnitude and are greatest for those vapor/GCNF combinations affording strong van der Waals or hydrogen-bonding interactions. A response value as large as $2\times10^5$ is observed for $NH_3$ vapor detection by GCNF-PAA/IDA sensors where strong hydrogen bonding between ammonia molecules and the carboxylic acid groups of the GCNF-polymer chains is expected. Cycling GCNF/IDA sensors between air and analyte vapor atmospheres produces cyclic response curves showing sensor response times on the order of seconds to a few minutes.

Sample Preparation and Characterization

Herringbone GCNFs having an average diameter of ca. 150 nm and micron-scale lengths were prepared in multi-gram quantities at 600° C. using a 7:3 Fe/Cu growth catalyst and a $C_2H_4/H_2/He$ (4:1:1) atmosphere following a modified literature procedure. Herringbone GCNF-PBA (11 wt % polymer) and GCNF-PAA (22 wt % polymer) polymer brushes were prepared from oxidized GCNFs using ester-coupling chemistry and atom transfer radical polymerization methods as described previously and isolated as dry, black powders. Amide coupling of 3,4'-oxydianiline to surface carboxylic acid sites present in oxidized herringbone GCNFs gave carbon nanofibers surface-derivatized with pendant amino functional groups, GCNF-ODA. Transmission electron microscopy (TEM) was performed on a Philips CM-20T Electron Microscope operated as 200 kV. Scanning electron microscopy (SEM) was performed on a Hitachi S-4200 Electron Microscope with an accelerating voltage at 1 kV to minimize sample charging effects.

Gas Sensor Measurements

GCNF samples to be tested as gas sensors were dispersed into acetone or water (GCNF-PAA). The resulting dispersion was dropped onto a multi-finger, interdigitated array (IDA) constructed of five parallel platinum metal lines (2.4 μm in both digit width and 5.6 μm interdigit spacing) printed on a glass substrate. Approximately, 1-3 mg of GCNF-polymer brush material was dispersed onto each fabricated IDA. IDA sensors were dried in air at room temperature for 24 h before electrical measurements were performed. Electrical resistance measurements were recorded at room temperature (28° C.) between the same two IDA poles using a digital Fluka True RMS Multimeter. IDA circuit resistance increased rapidly when fabricated GCNF/IDA sensors were placed into chambers saturated with analyte vapor and abruptly dropped to previous values when removed from analyte vapor and exposed to ambient air atmosphere. Resistance changes were recorded over several cycles of exposure to analyte vapor. Resistance responses were converted to sensor response values defined as $(R_v-R_0)/R_0$, where $R_v$ and $R_0$ are measured resistances in the presence and absence of analyte vapor, respectively. Ammonia vapor was obtained as the vapor head produced by a 29 wt % aqueous ammonia solution at room temperature.

Figure 31:
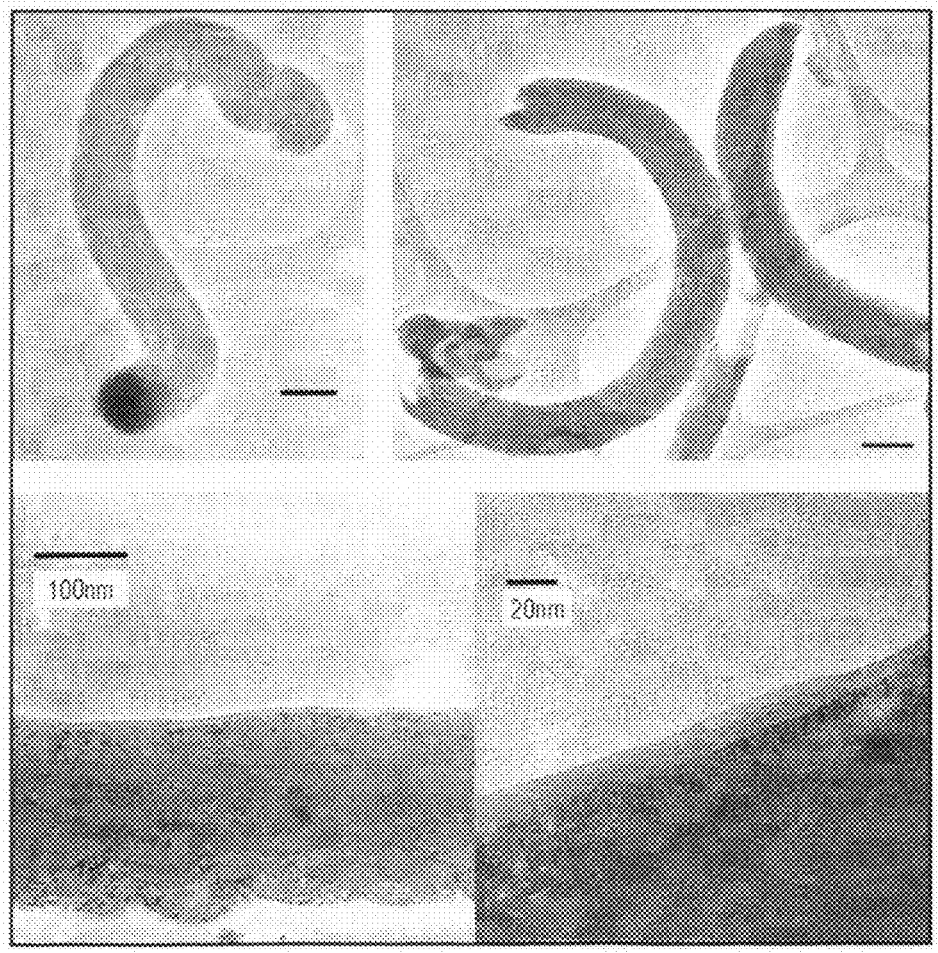
FIG. 31 illustrates TEM micrographs of as-prepared herringbone GCNFs (upper left; scale bar=200 nm), GCNF-ODA nanofibers (upper right; scale bar=200 nm), and GCNF-PBA polymer brush (lower images) at two magnifications showing the polymer brush component as a thin surface film.

As-prepared herringbone GCNFs have a nested "Dixie-cup" graphitic carbon nanofiber structure. Oxidation by nitric acid forms surface-oxidized GCNFs, $GCNF-CO_2H$, in which carboxylic acid groups are formed at nanofiber edge sites. Radical initiators covalently bound to these surface carboxylic acid sites by ester coupling chemistry initiate in-situ ATRP of acrylic acid ester monomers to give the corresponding GCNF/polymer brushes as dry, black powders. For the two GCNF-polymer brushes used in this study, the polymer chains have an average molecular weight of ca. 31,300 Daltons and a nanofiber surface density of ca. 3 polymer chains/10 $nm^2$. Transmission electron microscope (TEM) images of the various classes of GCNF materials used in this study are shown in FIG. 31.

Similarly, amide coupling of 3,4'-oxydianiline to surface carboxylic acid groups present in $GCNF-CO_2H$ nanofibers gives nanofibers surface derivatized with small-molecule oxydianiline amido functional groups, GCNF-ODA. The surface number density of ODA functional groups is ca. 2 molecules/10 $nm^2$, comparable to the areal surface functionalization present in GCNF-polymer brushes.

Figure 32:
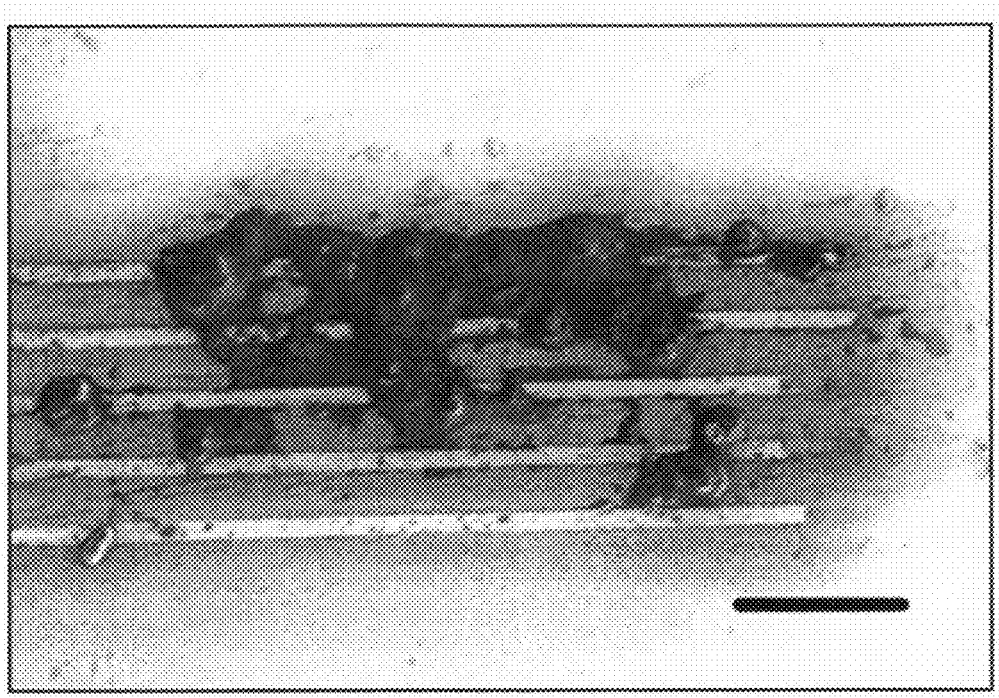
FIG. 32 illustrates an SEM micrograph of a fabricated GCNF/IDA sensor (scale bar=20 μm).
Figure 33:
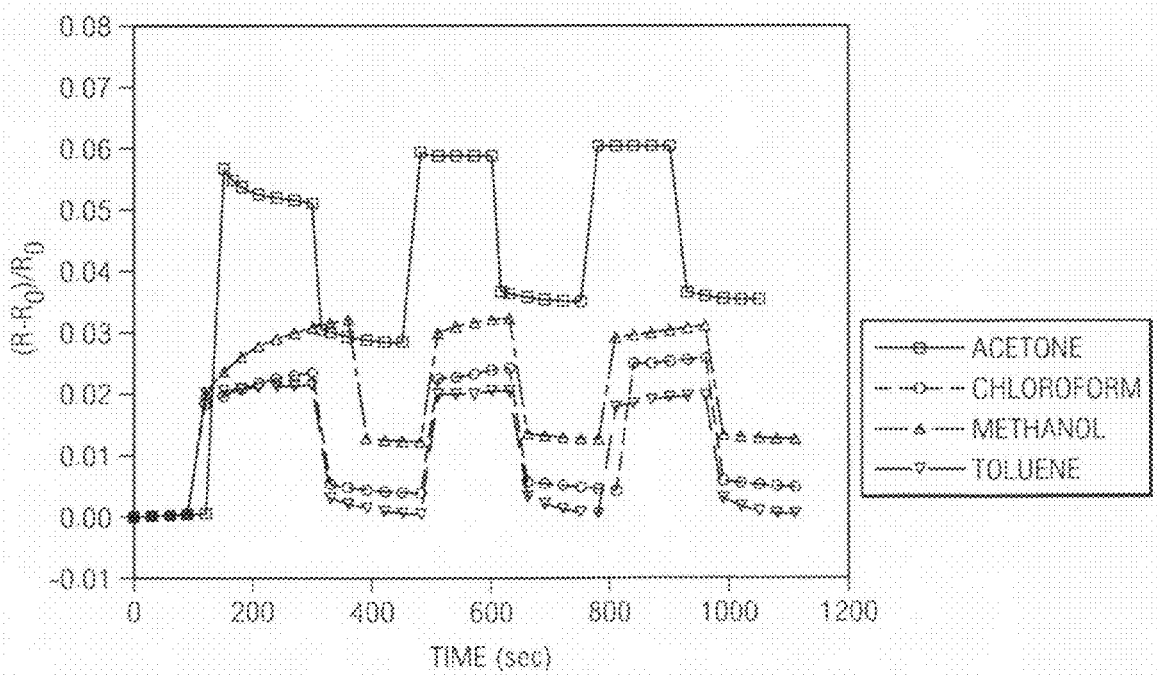
FIG. 33 illustrates an as-prepared GCNF sensor response cycled between ambient atmosphere and acetone, chloroform, methanol, and toluene saturated vapor atmospheres.
Figure 34:
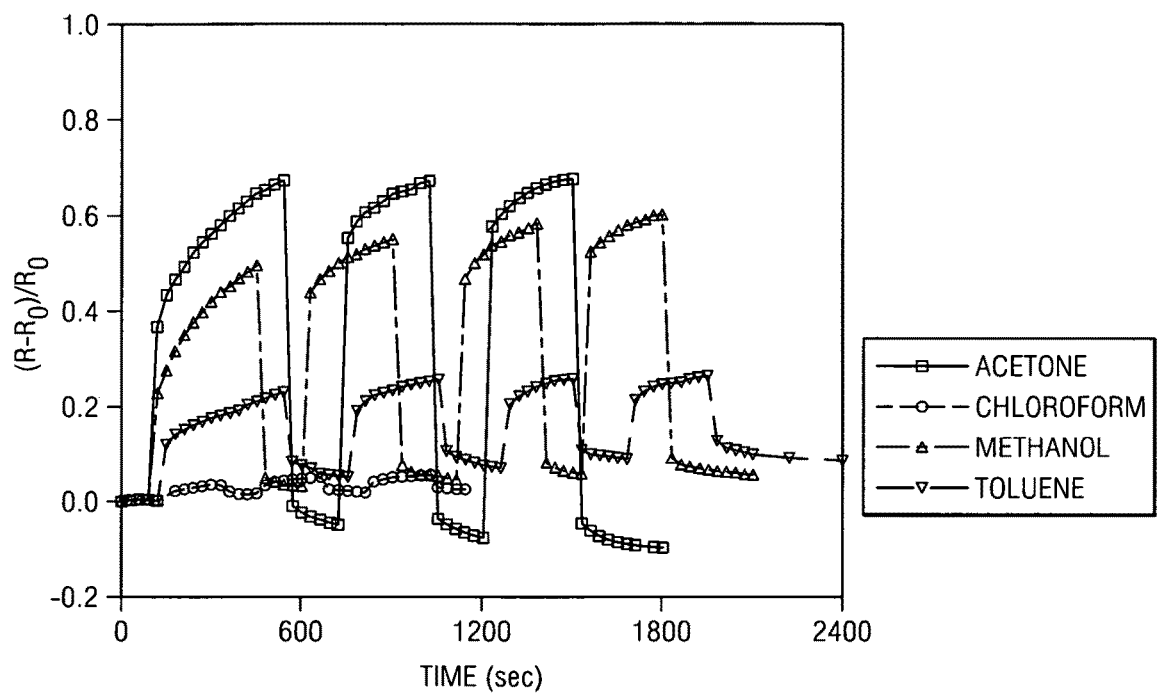
FIG. 34 illustrates GCNF-ODA sensor response cycled between ambient atmosphere and acetone, chloroform, methanol, and toluene saturated vapor atmospheres.

As-prepared GCNFs, GCNF-ODA nanofibers, and two GCNF-polymer brushes (GCNF-PBA and GCNF-PAA) have been evaluated as solid-state gas sensors. GCNF/IDA sensor circuits were fabricated by depositing the GNCF powder to be tested onto a Pt-wire IDA electrode (see FIG. 32). Sensor resistance was monitored digitally at room temperature while cycling the GCNF/IDA sensor between ambient air and saturated analyte vapor atmospheres. Gas detection was evident by an increase in sensor resistance. In related CNT/polymer composite gas sensors, increased electrical resistance upon exposure to analyte vapor has been attributed to matrix-swelling or CNT/adsorbate charge-transfer processes Resistance response values of GCNF/IDA sensors fabricated with as-prepared GCNF and GCNF-ODA nanofibers in the presence of various analyte vapors are shown in FIG. 33 and FIG. 34, respectively. Very low sensor response values (ca. $10^{-2}$) are observed for sensors fabricated with as-prepared GCNFs, but response values observed for sensors fabricated with GCNF-ODA powder are nearly 10 times greater. Analyte molecules interact more strongly with the molecularly derivatized GCNF-ODA surface than with the bare surface of as-prepared GCNF. A similar phenomenon has been observed with related carbon nanotube/polymer composite sensors. CNT/poly(methyl methacrylate) composite thin-film gas sensors exhibit higher resistance response values for those composites fabricated with surface-functionalized CNTs than those fabricated with bare as-prepared CNTs.

As-prepared GCNF/IDA and GCNF-ODA/IDA sensors both show chemoselectivity in analyte detection. As-prepared GCNFs show the greatest response to acetone vapor, significantly lower response to chloroform vapor, and markedly lower response to both methanol and toluene vapors. Since herringbone GCNFs possess a long-axis surface dominated by graphite edge sites, the adsorption characteristics of as-prepared GCNFs might be expected to mimic those of a graphite edge surface. Graphite edge surfaces are known to preferentially adsorb molecules of highest dipole moment. The chemoselectivity of as-prepared GCNF gas sensors revealed in FIG. 33 follows this same trend; [vapor (gas phase dipole moment in Debyes); acetone (2.88), methanol (1.74), chloroform (1.04), toluene (0.375)]. Especially strong adsorption of acetone vapor inhibits complete desorption of acetone between detection cycles.

A similar relationship between sensor chemoselectivity and analyte polarity is observed for GCNF-ODA/IDA sensors, except that the sensor response to toluene vapor relative to that of chloroform vapor is greater than that expected (FIG. 34). This effect probably results from favorable π-π van der Waals interactions between the aromatic rings of toluene analyte and the aromatic rings of surface-bound ODA molecules giving significantly enhanced response to toluene vapor. Increasingly more negative response recoveries observed for acetone as analyte might indicate trace formation of unsaturated "acetone anil" quinoline-based polymers that would slightly enhance conductivity at each subsequent recovery.

Sensor response times are quite abrupt and symmetrical for as-prepared GCNF nanofibers, but more gradual and asymmetrical for GCNF-ODA nanofibers. This observation is consistent with slower vapor adsorption/desorption kinetics expected for a molecularly derivatized nanofiber surface that interacts more strongly with gaseous analytes.

Figure 35:
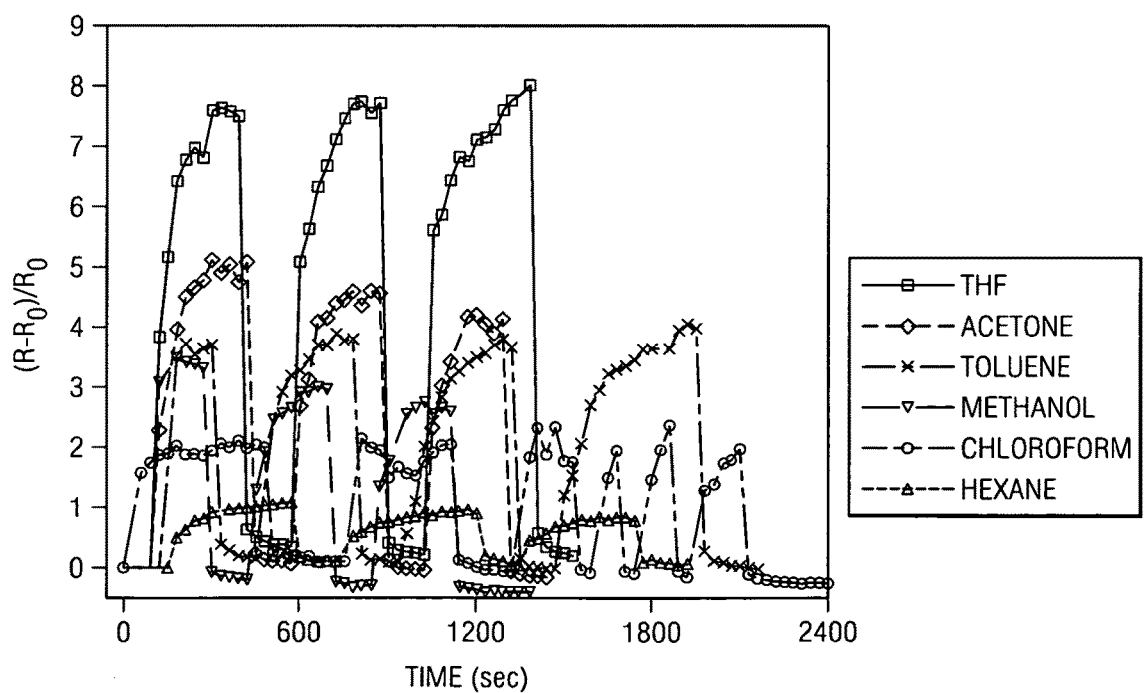
FIG. 35 illustrates GCNF-PBA sensor response cycled between ambient atmosphere and tetrahydrofuran (THF), acetone, toluene, methanol, chloroform and hexane saturated vapor atmospheres.

Larger sensor response values and enhanced analyte chemoselectivities are observed for organic vapor detection by GCNF-PBA polymer brush sensors (see FIG. 35). Maximum sensor responses are 10 times greater than those observed for GCNF-ODA nanofiber sensors and nearly 100 times greater than those observed for as-prepared GCNF sensors. Clearly, the presence of a surface-grafted polymer brush dramatically enhances the chemical sensing properties of GCNFs.

Analyte response sensitivities of GCNF-PBA sensors decrease as THF>acetone>toluene>methanol>chloroform>hexane in close correspondence with the known general solubility of pure PBA polymer in these respective solvent (except for the relative response to methanol vapor, see below). Solvent vapors of liquids known to be good solvents of pure PBA have greater tendencies to "wet" GCNF-PBA polymer chains, thereby increasing the detector resistance by a greater extent. Based on solubility parameter concepts, methanol should be the least wetting vapor of PBA polymer chains within this comparison and, therefore, the gas having the lowest sensor response value. The observed relatively high sensor response to methanol vapor has not been investigated in detail but could result from strong hydrogen bonding of methanol molecules to a small fraction of surface carboxylic acid groups that had not been completely derivatized by ATRP initiator molecules. GCNF-PBA/IDA sensor response times are quite abrupt for analyte desorption but more gradual for analyte sorption, as was observed for GCNF-ODA/IDA sensors, as well (FIG. 34).

In comparison, $CNT-CO_2H$/poly (methyl methacrylate) composite thin-film sensors show maximum resistance response values to organic vapors ranging over three orders of magnitude and response traces of similar shape. Vapor-grown carbon nanofiber/polystyrene composite films (with or without carbon black additive) exhibit maximum resistance response values over four to six orders of magnitude when exposed to organic vapors and response traces of similar shape during sensor cycling. Polyester-grafted carbon nanofiber/poly(ethylene glycol) composite thin-film sensors show a 100-fold increase in resistance upon exposure to THF vapor.

Figure 36:
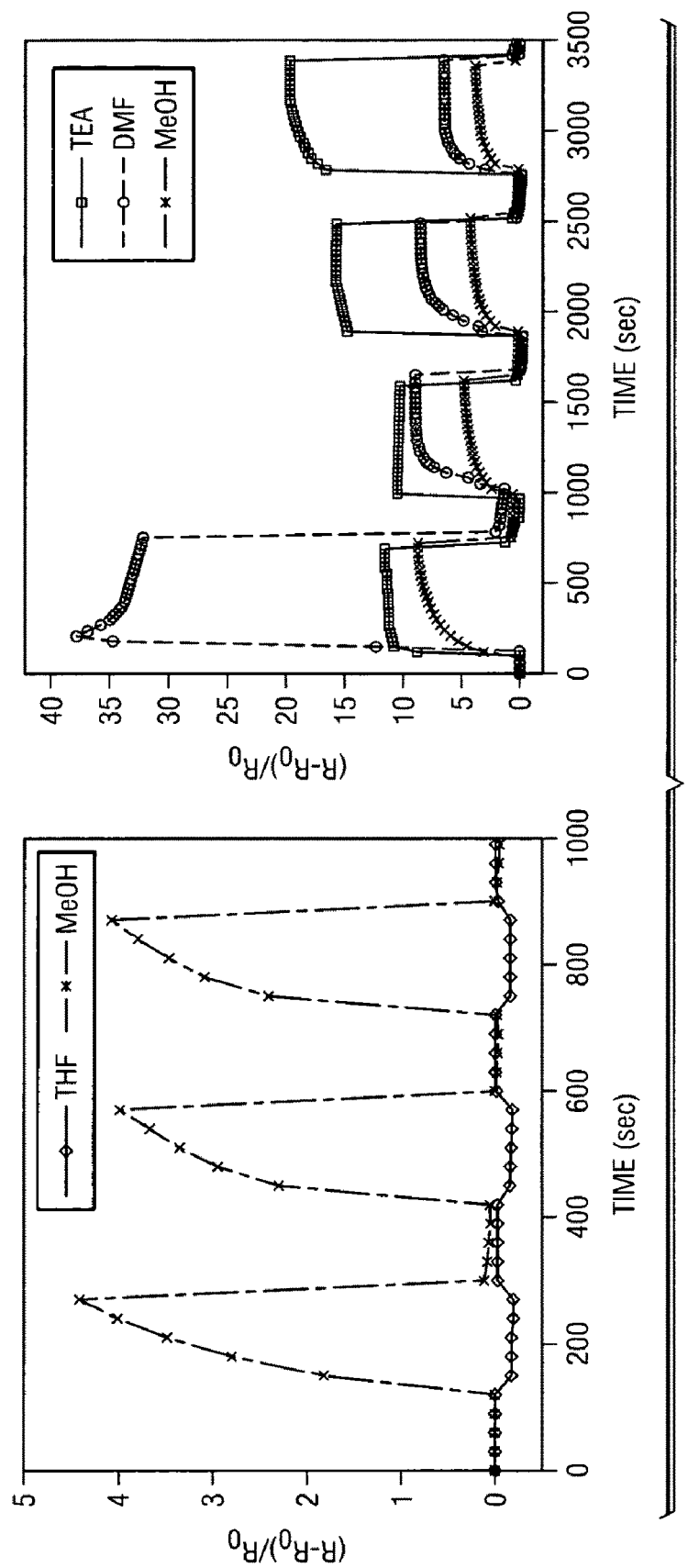
FIG. 36 illustrates GCNF-PAA sensor response cycled between ambient saturated atmospheres of triethylamine (TEA), dimethylforamide (DMF), methanol vapor (right), and tetrahydrofuran (THF) and methanol vapor (left; note change in response scale).

GCNF-PAA/IDA sensors show chemoselectivity and maximum response values for organic vapor sensing comparable to that observed for GCNF-PBA/IDA sensors (see FIG. 36). Initial-cycle sensor response values decrease as dimethylforamide DMF>triethylamine (TEA)>methanol>THF in close correspondence with the known decreasing solubility of pure PAA polymer in these respective solvents. Strong hydrogen bonding interactions between TEA, DMF, and methanol analyte molecules and carboxylic acid groups present in the PAA polymer brush chains affords large detector responses, while much weaker hydrogen bonding interactions with aprotic THF analyte molecules gives essentially a null response. DMF detection is unique in that the initial-cycle maximum response is ca. three times greater than that measured in subsequent cycles. The origin of this effect has not been investigated but clearly indicates some kind of polymer brush deactivation mechanism. Conversely, a slight increase in maximum response is observed for triethylamine analyte vapor detection over repeated cycles. A similar effect is observed with ammonia vapor detection (FIG. 37, vide infra) and suggests that trace retention of amine analyte might enhance analyte sorption in subsequent cycles by breaking up O—H . . . O hydrogen-bonding interactions between carboxylic acid groups within polymer chains.

Figure 37:
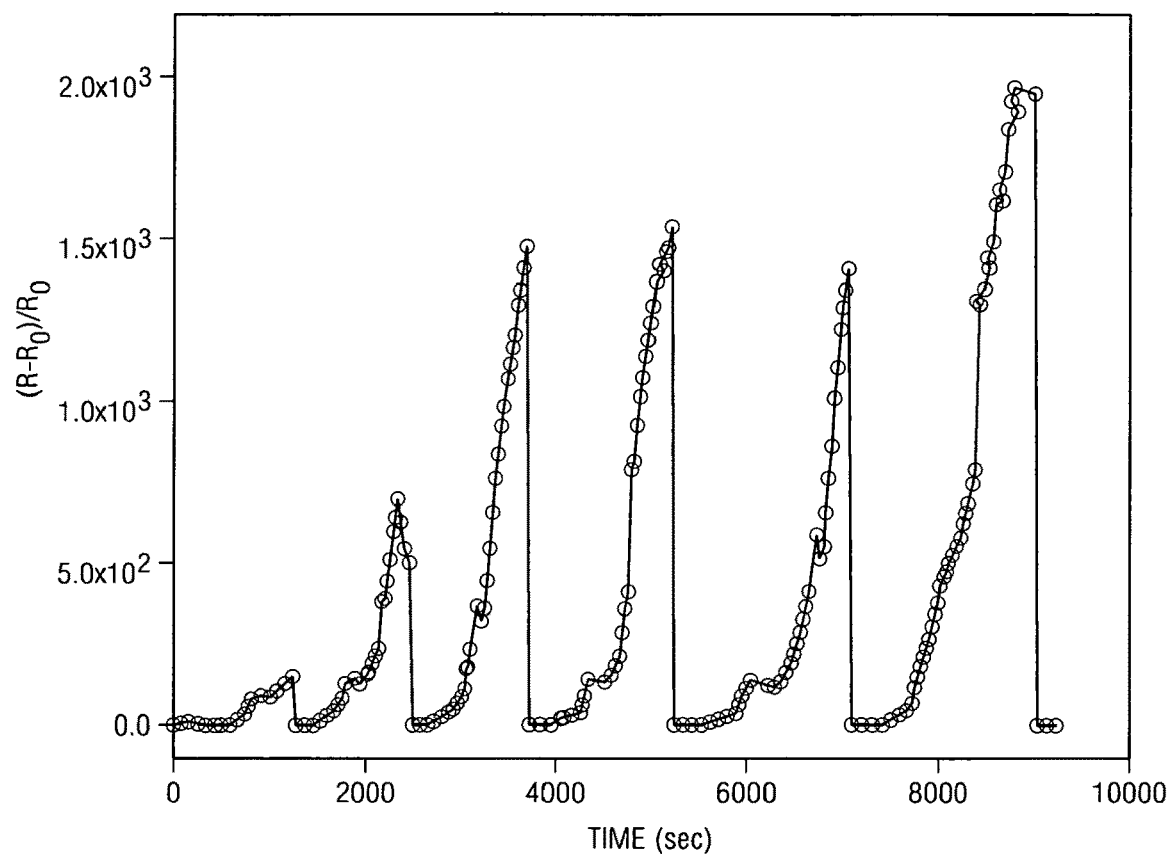
FIG. 37 illustrates GCNF-PAA sensor response cycled between ambient atmosphere and exposure to $NH_3$ vapor generated by 29 wt % aqueous ammonia.

However, when strong hydrogen-bonding interactions occur between an analyte gas and a GCNF-PAA polymer brush sensor, greatly enhanced maximum response is observed (see FIG. 37). GCNF-PAA/IDA sensing of $NH_3$ vapor occurs with maximum response values over 100 times greater than those observed for GCNF-PAA sensing of organic solvent vapors and nearly 1000 times greater than GCNF-PBA/organic vapor sensing. At least two sensing cycles are required to achieve this exceptionally high response for $NH_3$ detection. It is remarkable that $NH_3$ desorption occurs so rapidly and completely between each sensing cycle. Enhanced response and similar sensor cycling characteristics have been observed for ammonia detection by polyaniline thin-film gas sensors. The appearance of a peak in resistance ca. 12 min into each sensing cycle is curious. Since the vapor over aqueous ammonia solutions contain both water and ammonia, this feature might indicate kinetic resolution of both of these analytes.

Carbon nanofiber/IDA circuits fabricated with as-prepared herringbone GCNFs, GCNFs surface-derivatized with oxydianiline, GCNF-ODA, and poly(butyl acrylate), GCNF-PBA, or poly(acrylic acid), GCNF-PAA, polymer brushes unsupported by any polymer matrix act as solid-state gas sensors showing analyte chemoselectivity and response times ranging from seconds to several minutes. Sensor circuit resistance increases upon exposure to analyte vapor in parallel with the expected degree of vapor/sensor surface van der Waals interaction. GCNF-polymer brush sensors show maximum response values to organic vapors 10 times greater than those observed for GCNF-ODA sensors and 100 times greater than those observed for as-prepared GCNFs. Within each type of GCNF sensor, analyte chemoselectivity increases with the wetting ability of the analyte vapor. GCNF-PAA detection of $NH_3$ vapor occurs with maximum response ca. 1000 times greater than that observed for GCNF-PAA or GCNF-PBA detection of organic vapors, showing that strong hydrogen bonding between analyte molecules and GCNF-surface functional groups gives greatly enhanced sensor response.

By tailoring the chemical reactivity of GCNF-polymer brush functional groups to that of desired analytes, the fabrication of GCNF-polymer brush gas sensors having designed chemoselectivity is now feasible, thus permitting development of solid-state, multi-electrode arrays for gas sensing. The presence of a supporting polymer matrix is not required. Experiments investigating this possibility and determination of the intrinsic detection response of single GCNF-polymer brush nanofibers are underway.

DEFINITIONS

The term substantially is intended to mean largely but not necessarily wholly that which is specified. The term approximately is intended to mean at least close to a given value (e.g., within 10% of). The term generally is intended to mean at least approaching a given state. The term coupled is intended to mean connected, although not necessarily directly, and not necessarily mechanically. The term proximate, as used herein, is intended to mean close, near adjacent and/or coincident; and includes spatial situations where specified functions and/or results (if any) can be carried out and/or achieved. The term distal, as used herein, is intended to mean far, away, spaced apart from and/or non-coincident, and includes spatial situation where specified functions and/or results (if any) can be carried out and/or achieved. The term deploying is intended to mean designing, building, shipping, installing and/or operating.

The terms first or one, and the phrases at least a first or at least one, are intended to mean the singular or the plural unless it is clear from the intrinsic text of this document that it is meant otherwise. The terms second or another, and the phrases at least a second or at least another, are intended to mean the singular or the plural unless it is clear from the intrinsic text of this document that it is meant otherwise. Unless expressly stated to the contrary in the intrinsic text of this document, the term or is intended to mean an inclusive or and not an exclusive or. Specifically, a condition A or B is satisfied by any one of the following: A is true (or present) and B is false (or not present), A is false (or not present) and B is true (or present), and both A and B are true (or present). The terms a and/or an are employed for grammatical style and merely for convenience.

The term plurality is intended to mean two or more than two. The term any is intended to mean all applicable members of a set or at least a subset of all applicable members of the set. The phrase any integer derivable therein is intended to mean an integer between the corresponding numbers recited in the specification. The phrase any range derivable therein is intended to mean any range within such corresponding numbers. The term means, when followed by the term "for" is intended to mean hardware, firmware and/or software for achieving a result. The term step, when followed by the term "for" is intended to mean a (sub)method, (sub)process and/or (sub)routine for achieving the recited result.

The terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. The terms "consisting" (consists, consisted) and/or "composing" (composes, composed) are intended to mean closed language that does not leave the recited method, apparatus or composition to the inclusion of procedures, structure(s) and/or ingredient(s) other than those recited except for ancillaries, adjuncts and/or impurities ordinarily associated therewith. The recital of the term "essentially" along with the term "consisting" (consists, consisted) and/or "composing" (composes, composed), is intended to mean modified close language that leaves the recited method, apparatus and/or composition open only for the inclusion of unspecified procedure(s), structure(s) and/or ingredient(s) which do not materially affect the basic novel characteristics of the recited method, apparatus and/or composition.

Unless otherwise defined, all technical and scientific terms used herein have the same meaning as commonly understood by one of ordinary skill in the art to which this invention belongs. In case of conflict, the present specification, including definitions, will control.

The described embodiments and examples are illustrative only and not intended to be limiting. Although embodiments of the invention can be implemented separately, embodiments of the invention may be integrated into the system(s) with which they are associated. All the embodiments of the invention disclosed herein can be made and used without undue experimentation in light of the disclosure. Although the best mode of the invention contemplated by the inventor(s) is disclosed, embodiments of the invention are not limited thereto. Embodiments of the invention are not limited by theoretical statements (if any) recited herein. The individual steps of embodiments of the invention need not be performed in the disclosed manner, or combined in the disclosed sequences, but may be performed in any and all manner and/or combined in any and all sequences. The individual components of embodiments of the invention need not be formed in the disclosed shapes, or combined in the disclosed configurations, but could be provided in any and all shapes, and/or combined in any and all configurations. The individual components need not be fabricated from the disclosed materials, but could be fabricated from any and all suitable materials. Homologous replacements may be substituted for the substances described herein.

It can be appreciated by those of ordinary skill in the art to which embodiments of the invention pertain that various substitutions, modifications, additions and/or rearrangements of the features of embodiments of the invention may be made without deviating from the spirit and/or scope of the underlying inventive concept. All the disclosed elements and features of each disclosed embodiment can be combined with, or substituted for, the disclosed elements and features of every other disclosed embodiment except where such elements or features are mutually exclusive. The spirit and/or scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. A composition of matter comprising at least one herringbone graphitic-carbon-nanofiber/polymer brush,
    wherein there are covalently bound acrylate polymers located at, and directly connected to, carbon-atom surface sites on said at least one herringbone graphitic-carbon-nanofiber/polymer brush,
    wherein said at least one herringbone graphitic-carbon-nanofiber/polymer brush includes GCNF-poly(n-butyl acrylate), GCNF-poly(iso-butyl methacrylate), GCNF-poly(tert-butyl acrylate) or GCNF-poly(acrylic acid) and
    wherein an average surface density of polymer brush chains is at least approximately 3 polymer chains/10 $nm^2$.

2. A method of making a herringbone graphitic-carbon-nanofiber/polymer brush comprising covalently bonding a polymer to a surface of a herringbone graphitic-carbon-nanofiber by atom-transfer-radical-polymerization conducted employing grafted-from synthesis via atom-transfer-radical-polymerization initiators,
    wherein there are covalently bound acrylate polymers located at, and directly connected to, carbon-atom surface sites on the herringbone graphitic-carbon-nanofiber/polymer brush,
    wherein the herringbone graphitic-carbon-nanofiber/polymer brush includes GCNF-poly(n-butyl acrylate), GCNF-poly(iso-butyl methacrylate), GCNF-poly(tert-butyl acrylate) or GCNF-poly(acrylic acid) and
    wherein an average surface density of polymer brush chains is at least approximately 3 polymer chains/10 $nm^2$.

3. An apparatus gas comprising a gas sensor including at least one herringbone graphitic-carbon-nanofiber/polymer brush,
  wherein there are covalently bound acrylate polymers located at, and directly connected to, carbon-atom surface sites on said at least one herringbone graphitic-carbon-nanofiber/polymer brush, and
  wherein said at least one herringbone graphitic-carbon-nanofiber/polymer brush includes GCNF-poly(n-butyl acrylate), GCNF-poly(iso-butyl methacrylate), GCNF-poly(tert-butyl acrylate) or GCNF-poly(acrylic acid) and
  wherein an average surface density of polymer brush chains is at least approximately 3 polymer chains/10 $nm^2$.

* * * * *

UNITED STATES PATENT AND TRADEMARK OFFICE
CERTIFICATE OF CORRECTION

| | | |
|---|---|---|
| PATENT NO. | : 8,088,352 B2 | Page 1 of 1 |
| APPLICATION NO. | : 11/998470 | |
| DATED | : January 3, 2012 | |
| INVENTOR(S) | : Lukehart et al. | |

It is certified that error appears in the above-identified patent and that said Letters Patent is hereby corrected as shown below:

At column 35, line 7, delete "and".

Signed and Sealed this
Twenty-seventh Day of March, 2012

David J. Kappos
*Director of the United States Patent and Trademark Office*